(12) United States Patent
Lloyd

(10) Patent No.: US 10,639,390 B2
(45) Date of Patent: May 5, 2020

(54) SYSTEM AND METHOD FOR DISINFECTING AN OCCUPIED ENVIRONMENT USING DIRECTION CONTROLLED GERMICIDAL RADIATION

(71) Applicant: Ralph Birchard Lloyd, Fayetteville, NC (US)

(72) Inventor: Ralph Birchard Lloyd, Fayetteville, NC (US)

( * ) Notice: Subject to any disclaimer, the term of this patent is extended or adjusted under 35 U.S.C. 154(b) by 288 days.

(21) Appl. No.: 15/442,340

(22) Filed: Feb. 24, 2017

(65) Prior Publication Data

US 2017/0246329 A1 Aug. 31, 2017

Related U.S. Application Data

(60) Provisional application No. 62/299,827, filed on Feb. 25, 2016, provisional application No. 62/413,012, filed on Oct. 26, 2016, provisional application No. 62/413,029, filed on Oct. 26, 2016.

(51) Int. Cl.
 *A61L 2/10* (2006.01)
 *A61L 2/24* (2006.01)
 *A61L 2/08* (2006.01)

(52) U.S. Cl.
 CPC ............... *A61L 2/24* (2013.01); *A61L 2/084* (2013.01); *A61L 2/10* (2013.01); *A61L 2202/14* (2013.01); *A61L 2202/25* (2013.01)

(58) Field of Classification Search
 CPC ... A61L 2/24; A61L 2/10; A61L 2/084; A61L 2202/14; A61L 2202/25
 See application file for complete search history.

(56) References Cited

U.S. PATENT DOCUMENTS

| | | |
|---|---|---|
| 5,382,986 A | 1/1995 | Black et al. |
| 5,725,565 A | 3/1998 | Smith |
| 6,171,548 B1 | 1/2001 | Rose et al. |
| 6,656,424 B1 | 12/2003 | Deal |
| 6,911,177 B2 | 6/2005 | Deal |
| 7,175,806 B2 | 2/2007 | Deal et al. |

(Continued)

FOREIGN PATENT DOCUMENTS

| | | |
|---|---|---|
| CN | 205079861 U | 3/2016 |
| WO | 0160419 A1 | 8/2001 |
| WO | 2016061380 A1 | 4/2016 |

OTHER PUBLICATIONS

"Meet Kinect for Windows." 4 pages. Accessed Feb. 22, 2017 at https://developer.microsoft.com/en-us/windows/kinect. Microsoft.

(Continued)

*Primary Examiner* — Regina M Yoo
(74) *Attorney, Agent, or Firm* — NK Patent Law

(57) ABSTRACT

A system and method of disinfecting an area using germicidal radiation. The system is configured to capture images of an environment, analyze the images to determine locations of a person or unprotected skin of a person in the environment, and control one or more germicidal radiation emitters to decontaminate the environment where the person or exposed skin of persons in the environment are not located. The system and method allow for safe decontamination of an environment using hazardous levels of germicidal radiation while occupied by a person who may not be fully protected from the radiation.

9 Claims, 15 Drawing Sheets

(56) References Cited

U.S. PATENT DOCUMENTS

| | | | |
|---|---|---|---|
| 7,415,202 B2 | 8/2008 | Fujimoto et al. | |
| 7,692,172 B2 | 4/2010 | Leben | |
| 8,097,861 B2 | 1/2012 | Leben | |
| 8,127,396 B2 | 3/2012 | Mangiardi | |
| 8,294,580 B2 | 10/2012 | Witwer et al. | |
| 8,708,141 B1 | 4/2014 | Invie et al. | |
| 8,816,301 B2 | 8/2014 | Stibich et al. | |
| 8,842,019 B2 | 9/2014 | Boccola | |
| 8,877,124 B2 | 11/2014 | Bergman | |
| 8,907,304 B2* | 12/2014 | Kreitenberg | A61L 2/10 |
| 8,941,078 B2* | 1/2015 | Tantillo | A61L 2/10 |
| 9,023,274 B2 | 5/2015 | Garner et al. | |
| 9,034,271 B2* | 5/2015 | Shur et al. | B01J 19/12 |
| 9,345,798 B2 | 5/2016 | Trapani | |
| 9,358,313 B2 | 6/2016 | Deal | |
| 9,511,159 B2* | 12/2016 | Kreiner et al. | A61L 2/00 |
| 9,724,441 B2* | 8/2017 | Shur et al. | F24F 3/16 |
| 2007/0231192 A1 | 10/2007 | Jung et al. | |
| 2007/0231194 A1 | 10/2007 | Jung et al. | |
| 2009/0263499 A1 | 10/2009 | Platt, Jr. et al. | |
| 2011/0288617 A1 | 11/2011 | Sharma | |
| 2012/0075464 A1 | 3/2012 | Derenne et al. | |
| 2012/0126134 A1 | 5/2012 | Deal et al. | |
| 2012/0282135 A1 | 11/2012 | Trapani | |
| 2013/0296978 A1 | 11/2013 | Fiset | |
| 2015/0069270 A1* | 3/2015 | Shur et al. | A61L 2/10 |
| 2015/0258234 A1 | 9/2015 | Larsen | |
| 2015/0336014 A1* | 11/2015 | Stenzler | A63G 33/00 472/137 |

OTHER PUBLICATIONS

"Kinect for Windows Programming Guide." 2 pages. Accessed Feb. 22, 2017 at https://msdn.microsoft.com/en-us/library/dn782037(d=printer).aspx. Microsoft.

"Laser Show Projector Specifications." 8 pages. Jan. 13, 2017. Accessed Feb. 22, 2017 at http://lasershowprojector.com/laser-show-projector-specifications/ Projector Refferal Network Inc.

"Laser Show Projectors Explained." 8 pages. Jan. 13, 2017. Accessed Feb. 22, 2017 at http://lasershowprojector.com/laser-show-projectors-explained/ Pangolin Forum.

"Moving head laser projector LPS Impression Laser." 2 pages. Accessed Feb. 22, 2017 at http://www.lps-laser.com/laser-show-with-moving-head-laser-projector-glp-impression-laser.htm. LPS-Lasersysteme, Ofterdingen, Germany.

"LPS Impression Laser." Data Sheet. 1 page. Accessed Feb. 22, 2017 at http://www.lps-laser.com/download/data-sheet-datenblatt/moving-head-laser-projektor-GLP-impression-laser.pdf LPS-Lasersysteme, Ofterdingen, Germany.

"Implementing User Experience Guidelines in Intel® RealSense™ Applications." 9 pages. Jul. 8, 2016. Accessed Feb. 22, 2017 at https://software.intel.com/en-us/articles/implementing-user-experience-guidelines-in-intel-realsense-applications. Intel.

"Smartglasses." 11 pages. Accessed Feb. 22, 2017 at https://en.wikipedia.org/wiki/Smartglasses. Wikipedia, the free encyclopedia.

"Computer vision." 11 pages. Accessed Feb. 23, 2017 at https://en.wikipedia.org/wiki/Computer_vision. Wikipedia, the free encyclopedia.

"OpenCV." 4 pages. Accessed Feb. 23, 2017 at https://en.wikipedia.org/wiki/OpenCV. Wikipedia, the free encyclopedia.

Reed, N. G., "The History of Ultraviolet Germicidal Irradiation for Air Disinfection", Public Health Reports, Jan. 1, 2010, pp. 15-27, vol. 125, No. 1.

Memarzadeh, F., et al., "Applications of ultraviolet germicidal irradiation disinfection in health care facilities: Effective adjunct, but not stand-alone technology", Association for Professionals in Infection Control and Epidemiology, Inc., American Journal of Infection Control, Jan. 1, 2010, pp. S13-S24, vol. 38, No. 5.

International Search Report dated May 8, 2017 in re International Application No. PCT/US2017/019370 filed Feb. 24, 2017.

* cited by examiner

SYSTEM AND METHOD FOR DISINFECTING AN OCCUPIED ENVIRONMENT USING DIRECTION CONTROLLED GERMICIDAL RADIATION

RELATED APPLICATIONS

This application claims the benefit of U.S. Provisional Application No. 62/299,827 filed on Feb. 25, 2016, U.S. Provisional Application Nos. 62/413,012 and 62/413,029 each of which was filed on Oct. 26, 2016. Each of these applications is hereby incorporated by reference in its entirety.

BACKGROUND

Disinfection of areas of medical facilities is a key component to reduce or eliminate hospital acquired infections, also known in the art as nosocomial diseases or infections. The problem has become so serious that many medical facilities close or restrict areas to allow for intensive methods to eradicate the micro-organisms that cause these infections.

Germicidal radiation including ultraviolet radiation and more recently high intensity narrow spectrum (HINS) light have been found to be ways to treat these areas to reduce the levels of these micro-organisms. Ultraviolet germicidal irradiation is a disinfection method that uses ultraviolet radiation at a sufficiently short wavelength to break down these micro-organisms. Ultraviolet-C radiation with a wavelength of between 180-280 nm (and particularly between 240 nm-280 nm) has been found to be particularly effective. UV-B between 280-320 nm also has germicidal properties. The relatively short wavelengths of ultraviolet-C and B radiation are harmful to forms of life at the micro-organic level by destroying the ability of microorganisms to reproduce by causing photochemical changes in nucleic acids in these organisms so that their DNA and/or RNA chemical structure is disrupted. The disruption prevents micro-organisms from replicating, thereby rendering them inactive and unable to cause infection.

Disinfecting using ultraviolet radiation has been limited. This is mainly due to existing systems being configured to require the treated areas to be unoccupied by people. This precaution stems from the fact that UV exposure to unprotected skin can produce various negative effects including erythema, photosensitivity, skin aging, immune system damage, and even increased occurrences of skin cancer. The most serious effects of UV exposure are those which affect the eyes, the results of which can produce photokeratitis and conjunctivitis and other corneal injuries, including potentially cataracts in the eye lens. It so happens that the wavelengths most effective for germicidal uses are also the wavelengths that are most destructive to human tissue. Thus, these existing systems cannot be used in areas populated by people who are not properly protected from UV radiation. Or when used, their application is limited to relatively small physical areas such as unoccupied rooms, floors, ductwork, doorways, or ceilings or inside of air purifying devices and the like. Since the 1930's the use of UV radiation during surgeries has occasionally been practiced, but in these instances personnel in the area are fully protected from the UV with clothing, skin creams, and UV protective eyewear which is administratively controlled for the short duration of the surgery. More recently, UV radiation devices are being used to irradiate rooms in hospitals after patients are discharged or after surgeries are completed, so called "terminal cleaning," and studies are showing that when rooms are treated by UV radiation in this way that infection rates of subsequent occupants of the rooms are lowered. In all cases in the application of such germicidal radiation devices, persons are required to leave the room or environment to avoid being irradiated with harmful UV radiation. Overall, UV radiation systems are not conducive to treating areas in which people are routinely located, thus limiting the major benefits they can provide. UV radiation, with proper protection, can be superior to other forms of sanitation which are used to reduce microorganism populations, such as periodic cleanings with bleach or emitting a toxic chemical mist into the air. Being able to continuously irradiate an environment with germicidal radiation would have the most benefits. But the inability to ensure administratively that everyone in an area is properly protected at all times and for extended periods of time makes the continuous or semi-continuous use of UV decontamination in the presence of persons infeasible.

More recently, other wavelengths of radiation in the visible range have been found to have germicidal activity. High intensity narrow spectrum light (HINS) in the range of 380 to 420 nm, violet light, and particularly the 400-410 nm range centered on 405 nm, has been found to have some germicidal activity. Although these wavelengths are not harmful to humans as is UV radiation, because such high intensities are needed it would not be desirable to expose the unprotected human eyes to HINS.

Being able to expose environments to germicidal radiation without allowing the germicidal radiation to contact persons in the environment, or exposing the environment and persons in the environment to germicidal radiation after first electronically confirming that the persons in the environment are adequately protected from the germicidal radiation, is currently unknown. All known germicidal decontamination systems either go to great lengths to ensure that persons are not present in the environment when the radiation is emitted or assume that administrative procedures have been followed and are adequate to ensure that the person is fully protected.

SUMMARY

The present application includes a system which can electronically monitor persons in an environment and detect the persons and unprotected skin and eyes of persons. The system utilizes a beam of direction, intensity, and shape controlled germicidal radiation to expose those areas in the environment with protected skin and eyes to the germicidal radiation while at the same time avoiding exposing unprotected skin and eyes to harmful germicidal rays. The system may electronically monitor persons in an environment and detect whether or not persons in the environment have adequate skin and/or eye protection, and, if a person in the environment is found to not have adequate eye or skin protection, be able to change the direction and output or discontinue the output of the germicidal radiation to keep persons in the environment safe.

One aspect of the present application is directed to the use of current advancements in imaging, computer vision, smart technology, laser beam control technology, and other advanced technologies to manage the safety concerns of using germicidal radiation to decontaminate occupied environments, thereby allowing the use of continuous or semi-continuous germicidal radiation to kill or render incapable of reproduction microbes in an environment while patients, healthcare workers, and/or other persons are present in that environment. The benefits of this are: (a) microbes in the air, emitted by coughing or sneezing, can be killed before they spread, (b) microbes on surfaces can be killed before being transferred to others, (c) much more active, real-time decontamination can be occurring on a continuous basis rather than relying on periodic chemical cleaning techniques or infrequent UV "terminal" cleaning operations, (d) microbes on the clothing and, if adequately protected, the skin of the patients themselves or other persons can also be decontaminated, thereby helping to prevent the spread of diseases from the patient into the environment or from person to person. Other potential uses of this invention include but are not limited to decontamination of office spaces, governmental complexes, research facilities, portable emergency care facilities, nursing care facilities, homes, schools, food preparation facilities, emergency response vehicles, manufacturing facilities, and even outdoor environments where there is a concern about the spread of infectious diseases. It will be evident to those in the medical community that this invention has the potential to improve health care outcomes by reducing the number and severity of infections, reducing fatalities from hospital acquired infections, reducing health care costs, and reducing the potential for the development of anti-biotic resistant microorganisms, all of which are urgently needed in the health care system.

Another aspect is the system is configured to take images of an environment in which disinfection of microorganisms is desired. This can be done using cameras designed to capture images of the environment using visible light and using cameras designed to capture images using infrared light, ultraviolet light, other electromagnetic wavelengths, or combinations of these. The system then uses known "computer vision" programming techniques to identify areas in the image or images that represent persons and/or the exposed skin and head of persons in the images.

Once an image of the environment is obtained and analyzed for persons or the exposed skin and head of persons that might be present in the environment, a direction, intensity, and shape controlled beam of germicidal radiation can be emitted into the environment, usually from essentially the same position as the image was captured, the direction, intensity, and shape being controlled so that the germicidal radiation beam does not contact places where the persons or the exposed skin and head of persons in the environment are located.

This process of taking an image of an environment, analyzing the image to determine the location of the persons and/or the unprotected skin and heads of persons in the environment, and then projecting a beam of germicidal radiation into the environment to irradiate only those areas with no persons or unprotected skin and heads of persons ("safe" areas) while avoiding those areas with persons or unprotected skin and heads of persons ("unsafe" areas) can be repeated very rapidly, such that the beam of germicidal radiation is emitted throughout the environment faster than the persons in the environment are moving, thus ensuring that persons are not inadvertently exposed to harmful levels of radiation. Those skilled in the art of laser projectors and laser light shows will recognize the capability of galvanometer scanners, one of the means envisioned in this application to control the direction of the beam of germicidal radiation, to move the beam very rapidly or precisely project beams of radiation into an environment at rates of eight thousand to sixty thousand points per second to create an image on a screen, movements so fast that they are barely perceptible to the naked eye. Creating a system to very rapidly capture a digital image of an environment, analyze it with computer algorithms for the presence of persons or unprotected skin and heads of persons in the environment, and then decontaminate portions of the environment with a germicidal beam of energy controlled by galvanometer scanners or other rapidly responding direction control technologies is within the capabilities of today's technology. What has never been done before and has not been contemplated prior to this invention is the ability to combine these known technologies to control a beam of hazardous germicidal radiation to such an extent that it can be used to safely decontaminate occupied environments, even when persons in the environment are not fully protected from the hazardous germicidal radiation if it were to come in contact with their unprotected eyes or skin.

One embodiment is directed to a system for disinfecting an environment. The system includes an imaging system configured to capture an image of an environment and a germicidal radiation emitter that emits germicidal radiation into the environment. The system also includes processing circuitry configured to: analyze the image and determine an area within the environment either where a person is located or where exposed skin of a person in the environment is located; adjust at least one of a shape of a beam that is emitted by the emitter, an intensity of the germicidal radiation, and a direction of the germicidal radiation to prevent the germicidal radiation from being emitted into the environment in the area where the person is located or where the exposed skin is located and to emit the germicidal radiation into other areas in the environment.

The processing circuitry may be further configured to track movement of the person in the environment.

The processing circuitry may be further configured to detect whether the person in the environment is wearing eye protection and to prevent the emitter from emitting the germicidal radiation onto the person when the person is not wearing the eye protection.

The processing circuitry may be further configured to detect whether the person in the environment is wearing a protective coating on the exposed skin and to emit the germicidal radiation onto the exposed skin in response to determining that the protective coating is being worn.

The system may also provide for calibrating the direction that the emitter emits the germicidal radiation relative to the environment and the image that is obtained of the environment.

The imaging system may be configured to capture radiation that is within a range of wavelengths that correspond to the germicidal radiation that is emitted by the emitter.

The imaging system may include cameras configured to capture different wavelengths of radiation including at least two of ultraviolet, visible, and infrared wavelengths.

Another embodiment is directed to a system for disinfecting an environment. The system includes a germicidal radiation emitter that emits hazardous levels of germicidal radiation into the environment and at least one camera that captures an image of the environment. The system also includes processing circuitry configured to: analyze the image and determine a first area in the environment where the hazardous levels of the germicidal radiation can be emitted and cause the germicidal radiation emitter to emit the hazardous levels of the germicidal radiation in the first area; and analyze the image and determine a second area in the environment where a person is located and where less than the hazardous levels of the germicidal radiation can be emitted and cause the germicidal radiation emitter to emit less than the hazardous levels of the germicidal radiation in the second area.

The processing circuitry may be further configured to track the location of the person in the environment.

The processing circuitry may be further configured to detect whether the person in the environment is wearing eye protection and to prevent the emitter from emitting the hazardous levels of the germicidal radiation when the person is not wearing the eye protection.

The processing circuitry may be further configured to detect whether the person in the environment is wearing a protective coating on exposed skin and to cause the emitter to emit the hazardous levels of the germicidal radiation on the exposed skin in response to determining that the person is wearing the protective coating.

The processing circuitry may be further configured to monitor where the germicidal radiation is being emitted into the environment by analyzing additional images captured by the imaging system while the germicidal radiation is being emitted into the environment.

The imaging system may include cameras configured to capture different wavelengths including at least two of ultraviolet, visible, and infrared wavelengths.

Another embodiment is directed to a method of disinfecting an environment. The method includes determining a location of a person or unprotected skin of the person in an environment using computer analysis of images of the environment, and emitting germicidal radiation into the environment in areas where the person is not located or where there is no unprotected skin.

The method may also include tracking the location of the person as the person moves about the environment.

The method may include detecting that the person in the environment is not wearing eye protection and preventing the emission of the germicidal radiation where the person is located in the environment.

The method may include detecting that the person in the environment is wearing a protective coating on the exposed skin and emitting the germicidal radiation onto the protective coating on the exposed skin.

The method may include calibrating a direction that the emitter emits the germicidal radiation relative to the environment and the image that is obtained of the environment.

The method may also include capturing radiation that is within a range of wavelengths that correspond to the germicidal radiation that is emitted by the emitter.

The method may also include capturing images of the environment using multiple cameras and capturing different wavelengths of radiation including at least two of ultraviolet, visible, and infrared wavelengths.

The method may include monitoring a location of the germicidal radiation emitted into the environment by capturing images of the environment in the germicidal radiation wavelengths while the germicidal radiation is being emitted into the environment.

The method may include that the imaging system has cameras configured to record different wavelengths of radiation, with the cameras configured to capture at least two of ultraviolet, visible, and infrared wavelengths.

One embodiment of use includes a system or method of disinfecting an environment that includes: taking images of a patient's room in a hospital using both infrared and visible light cameras from essentially the same vantage point (infrared images may be particularly useful if the lighting in the room is low); analyzing the images to determine where from the perspective of the images the persons and heads or areas of unprotected skin of any persons who might be in the environment are and are not located, creating a two dimensional map of the environment within the borders of the images that delineate "safe" areas and "unsafe" areas, in response to determining where in the environment from the perspective of the image there are no areas of the person's head and unprotected skin (the so-called "safe" areas), rapidly scan and decontaminate the "safe" areas with one or more of a direction, intensity, and shape controlled beam of germicidal radiation controlled with a galvanometer scanner. The source of germicidal radiation in this embodiment could be a laser, an LED, a flash lamp, or other source with an output in the range of germicidal radiation wavelengths. The sequence of taking the image, analyzing the image, and decontaminating the "safe" areas is accomplished at least ten times per second in this embodiment.

It is advantageous that this system be provided a means of physically moving the imaging and disinfecting field of view, with up and down and side to side turning capabilities of the imaging and radiation emitting units. More range of motion and decontaminating angles can be achieved by for example mounting the system on a track hung from the ceiling or turning the system around on a vertical axis or up and down on a vertical support. Mounting the system on a robotic vehicle to decontaminate the environment from many angles would also provide greater flexibility in coverage area and is contemplated in this invention.

Another embodiment is directed to situations in which there are concerns that germicidal radiation may reflect off of objects in the area and onto unprotected eyes of persons in the environment. This embodiment includes a system or method that includes providing a means of determining whether persons in the environment are wearing eye protection; in response to determining that a person in the environment is not wearing eye protection, preventing the system that controls the germicidal radiation emitter from emitting germicidal radiation into the environment or modifying the decontamination protocol to protect the person not wearing the eye protection. The means for determining whether persons in the environment are or are not wearing eye protection could be switches or sensors located on the eye protection that sense the position of the eye protection relative to the person's body and thus determining whether or not the eye protection is being worn, the output from which could be wirelessly communicated to the control circuit controlling the germicidal radiation emitter. Other means for determining whether persons in the environment are wearing eye protection could be a computer analysis of the images, wherein the computer determines whether or not persons in the environment are wearing eye protection.

Another embodiment is directed to situations in which there are concerns that germicidal radiation may reflect off of objects and onto unprotected skin of persons in the environment. This embodiment of use includes a system or method provides a means of determining whether persons in the environment are wearing skin protection; in response to determining that a person in the environment is not wearing skin protection, preventing the system that controls the germicidal radiation emitter from emitting germicidal radiation into the environment or modifying the decontamination protocol to protect the person not wearing the skin protection. In this embodiment, skin protection could be either clothing or creams and lotions designed to protect the skin of persons in the environment from harmful germicidal radiation rays. Special pigments, dyes, or other compounds could be added to the radiation-blocking creams and lotions that would be particularly visible in the images and would enable the computer vision algorithms to differentiate between skin that is protected and skin that is not protected. In response to such an analysis, the system for decontaminating the environment could either be disabled as long as the person who has unprotected skin is in the environment, or the focused beam of germicidal radiation could be allowed to pass over the areas of skin that are protected by the cream or lotion but not the areas of skin that are not protected by the cream or lotion. If microbe-killing substances are also added to the lotion and persons in the environment are encouraged to regularly apply the lotion to their hands and exposed skin areas, in combination with the germicidal radiation emitted onto the lotion-coated skin, this embodiment has the greatest decontamination potential and should destroy more pathogenic microbes in an environment than any other embodiment mentioned herein.

More embodiments are described in the detailed description. The various aspects of the various embodiments may be used alone or in any combination, and multiple sources of different wavelength germicidal radiation can be used alone or in any combination, as is desired.

DETAILED DESCRIPTION

Figure 1:
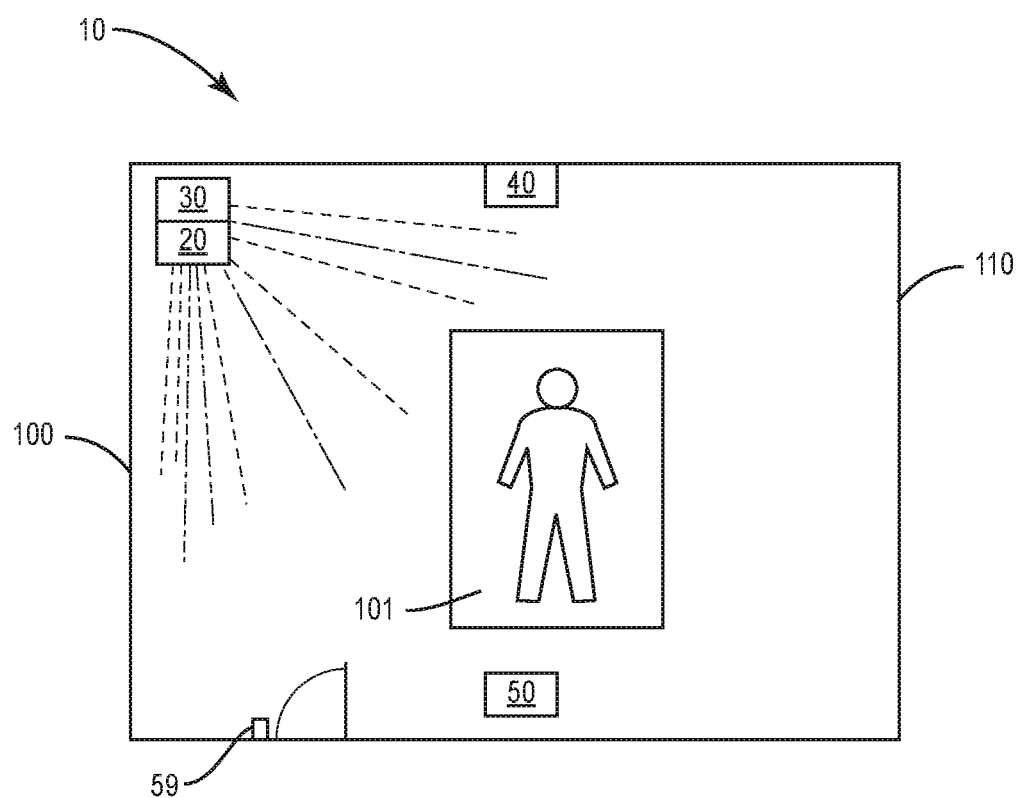
FIG. 1 is a schematic view of a system relative to an environment that includes a single section.

The present application is directed to systems and methods for disinfecting an environment using germicidal electromagnetic radiation including ultraviolet (UV) and/or HINS light radiation. Although some of the following description and majority of contemplated applications focus on UV radiation and emitters, it will be understood that HINS light or other germicidal radiation emitters can also be used in a similar manner to the embodiments described herein. The system includes a germicidal radiation emitter, usually an ultraviolet light or HINS light source, configured to emit a beam of ultraviolet or HINS radiation into an environment and to control the direction, intensity, and shape of the beam. The system also includes an imaging system, usually consisting of a camera or a camera system, to capture an electronic image of the environment. The system is equipped with computer algorithms to analyze the image from the imaging system to detect the presence and location of a person in the environment and/or the head area and unprotected skin of a person in the environment. The system then determines areas in the environment that are "safe" for emitting the beam of germicidal radiation and areas that are "unsafe" for emitting the beam of germicidal radiation, with "safe" being defined as areas where, if harmful levels of radiation were to be emitted from the emitter onto those areas, humans will not be harmed or receive a dose of germicidal radiation in excess of allowable radiation limits, and "unsafe" areas being defined as areas where, if harmful levels of radiation were to be emitted from the emitter onto those areas, humans might be harmed or might receive a dose of germicidal radiation in excess of allowable radiation limits. The primary safety concerns are exposure to the unprotected eyes and skin of persons in the environment. The system may further be equipped to detect how many persons are in the environment and where the persons in the environment are located. The system may further be equipped to determine whether the person is equipped with protective equipment such as eye protection (e.g. safety glasses or goggles) or skin protection (e.g. coatings on the skin to protect the skin from the germicidal radiation) and to determine where and how the output and direction of the emitter should be directed to emit harmful levels of germicidal radiation into the environment onto the "safe" areas while not exposing the "unsafe" areas to germicidal radiation. Based on these inputs, the processing circuitry 51 is configured to control at least one of the direction, intensity, and shape of a beam of germicidal radiation and emit it into the environment onto areas or surfaces determined to be "safe" but not onto areas or surfaces determined to be "unsafe" for exposure to the germicidal radiation. In some embodiments, areas determined to be "safe" for exposure include areas where there are no persons located or in other embodiments areas where there are no heads of persons in the environment (to avoid inadvertent exposure to the eyes) or areas of unprotected skin of persons in the environment. Thus, in some embodiments, areas of the persons in the environment which are covered by clothing or protective equipment may be exposed to the germicidal radiation. The processing circuitry 51 then may move the viewing angle and repeat the process for another area in the environment or may maintain the same viewing or imaging area of the environment and repeat the cycle on a periodic basis or both. The areas that are known by the analysis of the images to be "safe" are decontaminated in this manner; areas outside the image(s) or outside the ability of the processing circuitry 51 to confirm whether or not the areas are "safe" for decontamination are not decontaminated. The decontamination using the controlled direction, shape, and intensity of germicidal radiation should occur soon after the image is analyzed, as movement of persons in the environment continually create changes in where the "safe" and "unsafe" areas are located.

The systems and methods monitor one or more persons that are in an environment equipped with the one or more germicidal radiation emitters. This environment is treated with germicidal radiation, including when the one or more persons are present. The treatment may include emitting germicidal radiation onto the one or more persons that are present. The systems and methods may monitor the person(s) in the environment and/or the unprotected skin and head areas of the person(s) in the environment, determine whether the person(s) is protected from germicidal radiation, and control at least one of the direction, intensity, and shape of the germicidal radiation emission so that it does not fall on (or irradiate, shine on, contact, etc.) the person(s) in the environment and in other embodiments so that it does not fall on unprotected areas of person(s) in the environment. The systems and methods may monitor the location of a person(s) in the environment and the position of their bodies. The systems and methods may monitor the protective equipment of a person(s) in the environment, such as eye protection and skin protection, and ensure that the protective equipment is donned properly prior to allowing germicidal radiation to be emitted into the environment. The monitoring ensures that the one or more persons in the environment are protected from being exposed to unsafe levels of germicidal radiation depending upon one or more factors. The system is needed because levels of germicidal radiation that are effective for disinfection are typically far in excess of the allowable exposure limits for human eyes and skin. Controlling at least one of the direction, intensity, and shape of a beam of germicidal radiation is the ability to selectively emit germicidal radiation directly onto certain areas (or surfaces) in an environment and not emit germicidal radiation directly onto other areas in an environment in response to the automated computer analysis of an image or images of the environment. The term "image" means a two or three-dimensional array of electronic information from which the relative spatial locations of objects or surfaces in a field of view can be determined. The term "control" means the computer in the system is equipped to change the direction and/or intensity of the germicidal radiation emissions in response to an analysis of images of an environment processed by preprogrammed computer algorithms; not emitting any radiation from emission sources in response to an analysis of images of an environment is included in the definition of controlling the intensity of the germicidal radiation. Various electromechanical or other means can be provided to enable the computer to control the direction and intensity of radiation by the emitter. The control of the direction of germicidal radiation is not static but dynamic, being checked at regular intervals and changed as required, sometimes multiple times per second. Thus, objects in an environment that are not exposed to germicidal radiation at one point in time may be exposed to germicidal radiation at other times as a result of changing inputs and computer analyses. Radiation sources and devices in this application have the ability and corresponding control systems to be able to directly illuminate some areas of an environment without directly illuminating other areas of the environment and to be able to change the areas that are illuminated over time in response to what is happening in the environment in order to ensure the safety of persons in the environment, usually while at the same time decontaminating some parts of the environment.

FIG. 1 illustrates a schematic diagram of a disinfection system 10. The system 10 is designed for use with a predetermined environment 100. The system 10 includes a germicidal radiation emitter 20 equipped with a mechanism to control at least one of the direction, intensity or shape of the radiation emitted, resulting in a direction, intensity, and shape. The germicidal radiation may include one or more of UV-C, UV-B, and HINS radiation. An imaging system 30, which may include a camera or plurality of cameras which may include visible, infrared, and ultraviolet cameras and infrared laser scanners for depth measurements, is configured to take images of the environment 100 so that computer analysis of the image by a computing device 50 that includes processing circuitry 51 will determine where a person in the environment 100 is located and/or where the unprotected skin and head of a person in the environment is located. Sensor 40 is optional and is configured to track persons in the environment 100 or detect whether the persons in the environment are equipped with protective equipment such as eye protection or skin protection. Sensor 40 could be a sensor, a plurality or network of sensors, a camera, or a plurality or network of cameras. Sensor 40 is in communication with the processing circuitry 51. Imaging system 30 and sensor 40 could be a single sensor or a camera or a plurality of sensors or cameras or both. Processing circuitry 51 receives signals from the imaging system 30 and sensor 40, analyzes the images for persons, unprotected skin, and head areas, and then operates the emitter 20 in a manner that directs the radiation to areas and surfaces in the environment that do not contain unprotected skin of persons in the environment, the "safe" areas. In some embodiments, processing circuitry 51 operates the emitter 20 to avoid exposing parts of persons present in the environment to germicidal radiation.

In some embodiments, the emitter 20 and the imaging system 30 are located close to one another so that the radiation can be emitted from essentially the same perspective of the image, which is the basis on which the analysis for "safe" and "unsafe" areas is being done. The emitter 20 and imaging system 30 can be in a fixed location, but one or more of these components may be positioned on a support that is able to rotate and/or point the components in different directions within an environment to decontaminate the environment from a different viewpoint. In some embodiments, emitter 20, imaging system 30, and processing circuitry 51 are packaged in the same housing.

FIG. 1 and the following discussion include a computing device 50 with processing circuitry 51 that monitors a single person in the environment 100. The processing circuitry 51 may be configured to monitor multiple people in the environment 100 and operates in a similar manner. Further, the system 10 may include one or more of any of the various system components including an emitter 20, imaging system 30, and person tracking or protective equipment sensor 40. Further, sensors 30, 40 may be combined into a single component.

Figure 2:
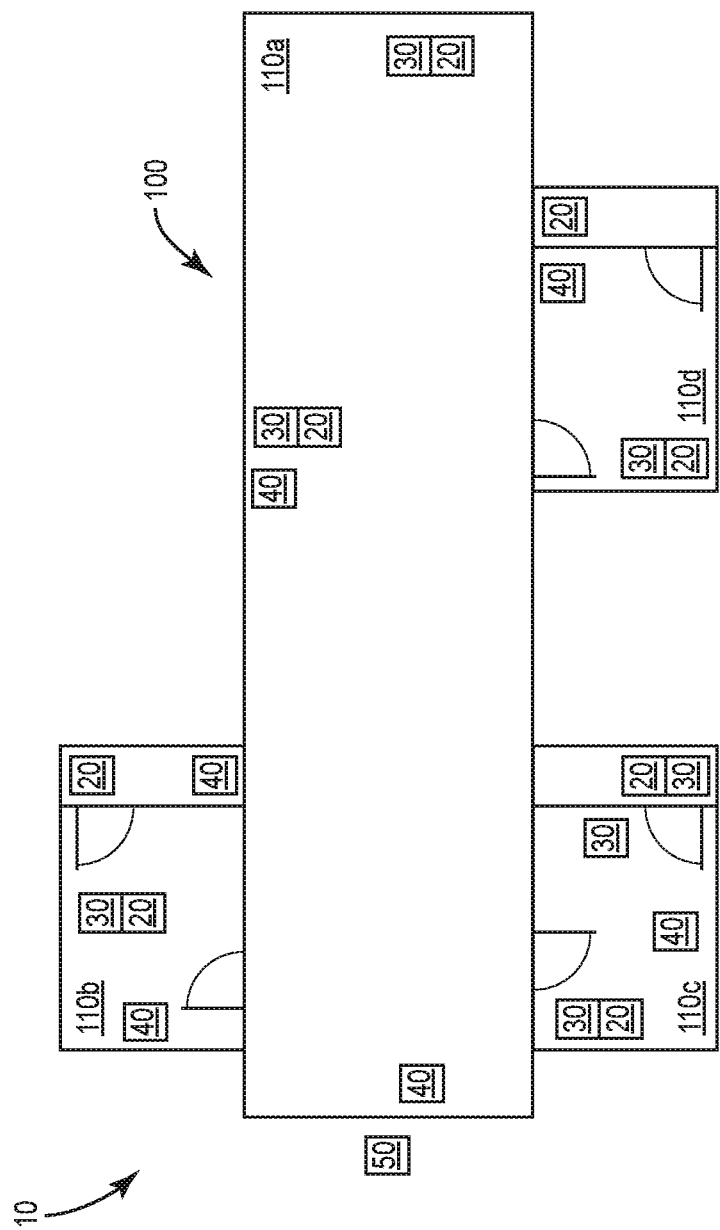
FIG. 2 is a schematic view of a system relative to an environment that includes multiple sections.

FIG. 1 includes the environment 100 being a single room, such as a hospital room or operating room of a medical facility. The system 10 is also applicable for use in a wide variety of environments having various shapes and sizes. Examples include an environment with multiple rooms, an entire hospital wing, a hospital floor, an entire hospital, an office or office building, a cafeteria of a school with multiple rooms, and an entire school. FIG. 2 illustrates the system 10 within a larger environment 100 that include four sections 110a-110d. Further, rooms 110b-d include two independent rooms (such as a hospital room with an adjoining bathroom). One example of such an environment is a hospital wing that includes a main hallway (such as section 110a) and separate patient rooms (sections 110b-d).

Figure 3:
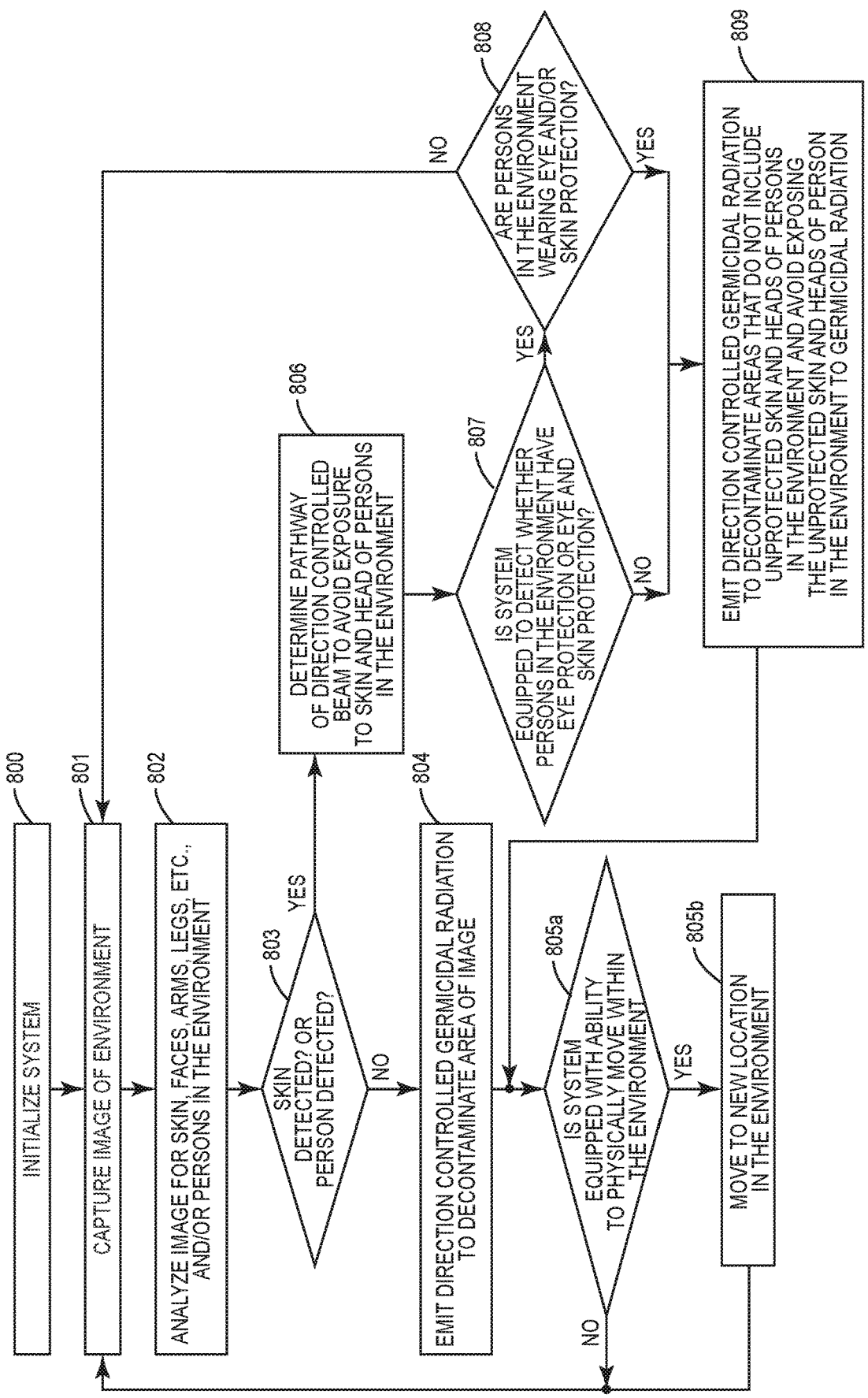
FIG. 3 is a flowchart diagram of a method of sanitizing an area using germicidal radiation.

FIG. 3 illustrates a method of system operation to disinfect an environment 100 using germicidal radiation. The method includes initializing the system 10 and ensuring the various components are in proper operating condition (block 800). Once the system 10 is initialized, the camera system 30 captures an image of the environment (block 801), and the processing circuitry 51 determines whether a person and/or whether exposed skin and head areas are in the portion of the environment 100 that is represented by the image (block 802). If no person is detected (block 803), the system emits into the environment and onto the area represented by the image or a portion of the image a predetermined amount of germicidal radiation per a predetermined pattern for when persons are not in the area of the image (block 804). If a person or exposed skin is detected (block 803), the processing circuitry 51 then determines the location of the person or the exposed skin of the person and clearly delineates where the "safe" areas and "unsafe" areas are in the environment from the perspective of the image. The processing circuitry 51 then determines a pathway for exposing "safe areas" of the image to direction controlled germicidal radiation from the emitter 20 while not exposing the "unsafe" areas to germicidal radiation (block 806). Optionally, if the system 10 is equipped with sensors 40 to determine whether persons in the environment have eye protection or eye and skin protection (block 807), the processing circuitry then checks for eye or eye and skin protection (block 808). If the system 10 is equipped with eye or eye and skin protection detection and it detects a person in the environment is not wearing the protection, then the system 10 does not emit radiation into the environment (other embodiments may take other action if there are unprotected persons in the environment) but repeats the cycle of capturing and analyzing images of the environment. If the processing circuitry 51 determines the person(s) in the environment has eye protection or eye and skin protection (block 808), or if the system 10 is not equipped to detect eye or eye and skin protection (block 807), the system 10 proceeds to emit direction controlled germicidal radiation into the environment onto areas that do not include unprotected skin and heads of persons in the environment ("safe areas") and avoid exposing unprotected skin and hands of persons in the environment to germicidal radiation ("unsafe areas") (block 809). If the system 10 is equipped with a mechanism for physically changing the location or vantage point of the system (block 805a), the system is pointed or moved to a new location in the environment (block 805b), and the sequence is repeated.

The disinfection system 10 is particularly applicable to a medical facility, such as a hospital, doctor's office, nurse's station, etc. The system 10 is also applicable to other settings, such as schools, office buildings, retail stores, shopping centers, nursing homes, rehabilitation facilities, biological research facilities, food preparation facilities, private homes, manufacturing facilities, and various other locations and populated environments where protection from micro-organisms that cause illness and harmful germicidal radiation are required. The hoped-for benefits of using smart technology to monitor individuals in a germicidal radiation environment is to enable persons to be kept safe while allowing the germicidal radiation to be emitted and therefore achieving more or less continuous disinfection of the environment.

Germicidal radiation has been found to be one way to treat environments (including but not limited to rooms, surfaces, air, and liquids in the environment) to reduce the level of micro-organisms, including but not limited to bacteria, viruses, and fungi. This includes ultraviolet germicidal irradiation which is a disinfection method that uses electromagnetic ultraviolet radiation at a sufficiently short wavelength to break down these micro-organisms. Ultraviolet-C radiation with a wavelength of between 180-280 nm (and particularly between 240 nm-280 nm) has been found to be particularly effective. UV-B between 280-320 nm also has germicidal properties. The relatively short wavelength of ultraviolet-C and B radiation is harmful to forms of life at the micro-organic level because it destroys the organism's ability to reproduce by causing photochemical reactions in the nucleic acids in their DNA and/or RNA chemical structure. This disruption prevents micro-organisms from replicating, thereby rendering them inactive and unable to cause infection. The combination of multiple wavelengths is more effective against some micro-organisms due to the ability of some microorganisms to repair damaged DNA from single wavelength UV radiation but not multiple wavelengths due to the fact that different UV wavelengths create different types of photo-initiated damage to the DNA that make it less probable that the organism can repair all types of damage simultaneously. Conversely, UVA radiation between 320-400 nm has fewer germicidal benefits, and therefore germicidal radiation is contained in the UVC and UVB bands. Germicidal radiation may also include high intensity narrow spectrum light (HINS) in the range of 380 to 420 nm, violet light, and particularly the 400-410 nm range centered on 405 nm, which has been found to have some germicidal activity.

The term "germicidal" implies the radiation destroys, kills, or inactivates microorganisms such as viruses, bacteria, and fungi (viruses are molecules, and so it is customary to refer to viruses as being inactivated rather than killed). In the present application, the term "disinfecting", "disinfection", and the like includes germicidal action that reduces a microbial population, as well as germicidal action that eliminates a microbial population.

A variety of different emitters 20 may be used in the system 10, and may have a variety of sizes and shapes. The germicidal radiation emitters 20 may emit continuous UV radiation or intermittent or pulsed UV radiation, sometimes referred to flashtubes or flashlamps. The emitter 20 may include a high intensity discharge lamp (also called high pressure or medium pressure mercury vapor lamps) and low pressure mercury vapor lamps. The emitter 20 may include PUV xenon lamps (pulsed high power xenon lamps producing broad spectrum 100-1000 nm light with a high UV-C component), and excimer lamps. Discharge lamps are lamps that generate UV radiation by means of an internal electrical discharge between electrodes in the presence of a gas. The term encompasses gas discharge lamps, which generate UV radiation by sending an electrical discharge through an ionized gas, and surface discharge lamps, which generate UV radiation by sending an electrical discharge along a dielectric surface in the presences of a gas, producing a plasma along the substrate's surface. Discharge lamps may be further characterized by the type of gas or gases used and the pressure at which they are operated. The discharge lamps may be low pressure, medium pressure, or high intensity. The gases may include but are not limited to helium, neon, argon, krypton, xenon, nitrogen, oxygen, hydrogen, water vapor, carbon dioxide, mercury vapor, sodium vapor, or combinations thereof.

A commonly used gas-discharge lamp used to produce continuous light is a mercury-vapor discharge lamp, which emits a strong peak of 253.7 nm radiation, which is particularly effective for use in germicidal disinfection. Another commonly used UV lamp for germicidal disinfection is a xenon flashtube, which emits a broad spectrum of UV light in the entire spectrum known to be germicidal (both UV-C and UV-B, between approximately 200 nm and 320 nm). Low pressure mercury vapor lamps emit almost exclusively UV-C radiation. Emitter 20 may also be an ultraviolet light emitting diode (UV LED). A UV LED emitter 20 may be configured to emit a narrow band of UV-C radiation at almost exactly the peak of germicidal effectiveness. A UV LED emitter 20 includes LED's that may include various configurations, such as a standard bulb type LED, a flat circle LED, and a rectangle LED. The UV LED emitter 20 may include a bank of LEDs. The LEDs may be mounted in a single bank of LEDs or strips of LEDs that each includes multiple LEDs. Specific embodiments may include LEDs mounted in a relatively flat arrangement or in strips, or rectangular arrays such as a picture frame and hung on walls or on the backs of doors. The emitter 20 may also be a plasma arc flash. The emitter 20 may be multiple emitters of the same or different types.

The emitter 20 may also be a High Intensity Narrow Spectrum (HINS) light emitter, which typically is constructed of LEDs emitting visible light in the violet and blue light range between 380 and 420 nm, usually centered on 405 nm.

The emitter 20 may also be a laser; multiple types of lasers and emitters could be considered that emit wavelengths of radiation with germicidal properties. For example, excimer lasers (e.g. ArF at 193 nm, KrCl at 222 nm, KrF at 248 nm, XeCl at 308 nm, etc.), Nd:YAG lasers (e.g. 5th harmonic at 213 nm, 4th harmonic at 266 nm, etc.), He-Ag+ (224.3 nm), Ne-Cu+ (248-270 nm), He-Au+ (282-292 nm), Ti:sapphire (tripled, 235-330 nm), or any combinations of these and other germicidal wavelength emitting lasers in the 190-430 nm range could be used. Lasers are well suited to this application because of their low diffusion and the ability to put the beam precisely where it is required over long distances. The diffusion of radiation from the radiation source 20 is an important factor to measure, as radiation sources with lower diffusion enable more precise control of the direction of the beam and can be brought closer to the boundaries between "safe" and "unsafe" areas, resulting in a higher degree of safety and confidence that "unsafe" areas are not being exposed to harmful levels of germicidal radiation plus the benefits of a more thorough decontamination. The importance of using sources of radiation with low diffusion increases with larger environments and increasing distance from the emitter to the areas being decontaminated. Examples of light sources that can project a beam of light long distances with low amounts of diffusion are search lights, spot lights, and lasers; the beams of light in these examples is still defined even after traveling distances of many meters due to low diffusion characteristics.

Diffusion is a measure of the tendency of the edges of a beam of electromagnetic radiation to blur and become fuzzy the further the beam gets from the source and is usually measured in milliradians or mrads (one thousandth of the radius of a circle when that radius is superimposed on the circumference of that circle; one milliradian approximately equals≈0.057296°; putting this into perspective, a divergence of a light beam of 0.1 mrad equals about 1 cm at 100 meters.)

In some embodiments, where a low diffusion beam of radiation is needed, ideally the emitter 20 will produce a beam with a diffusion of less than 100 milliradians, but sources with larger values of diffusion can also be useful. Although low diffusion is preferable, the amount of diffusion of the beam can be compensated for by the processing circuitry 51 if the amount of diffusion is known. If the beam has a low amount of diffusion, like a laser, it can be directed by the processing circuitry into the environment with great precision, with the area of the beam known to be comparable to the original source beam since the beam will not spread out significantly over the short distances of a room or hallway where this invention will find its greatest uses. In cases of a more diffuse beam, however, the processing circuitry 51 can be programmed to compensate for the larger diameter of the more diffuse beam as it is projected out into the environment and adjust the decontamination pattern of the more diffuse beam of germicidal radiation to keep it away from the "unsafe" areas of the environment. Thus, a lager margin of error is needed when controlling a more diffuse beam than when controlling a less diffuse beam. A more diffuse beam will also result in less efficient decontamination of the area since the greater the diffusion of the beam and the larger the resultant area of the beam when it falls on surfaces in the environment, the less the beam will be able to be used to decontaminate close to the edges of the "safe" areas for fear of it crossing over into the "unsafe" areas. Also, a more diffuse beam will result in lower intensity of radiation on the surfaces it contacts, and therefore the decontaminating effects will be less; in such cases the processing circuitry 51 may need to extend the time that the beam is emitted onto areas further away or make multiple passes or both.

The diffusion of radiation can be controlled in a variety of manners. One manner of controlling and minimizing the diffusion of beams of light is to provide a wave guide on the output of a source of radiation in which the length of the waveguide is significantly longer than its diameter, preferably a waveguide coated on the inside with a material reflective to the radiation being conducted (aluminum is one of the better metals suitable for ultraviolet radiation reflection). Lasers naturally produce a focused beam of light with very little diffusion, but the radiation output of other germicidal radiation emitters (e.g. discharge lamps, LED's, etc.) is more diffuse. However, the diffuse output of these sources can be collected and channeled into a narrow beam of non-diffuse light by means known in the art. Such means can include mirrored cavities and surfaces specifically designed to contain and channel radiation to a single narrow opening. Non-imaging or anidolic optical devices (e.g. light tubes, light guides, non-imaging reflectors and lenses, etc.) and fiber optics have also been used to create a focused beam of radiation from a diffuse light source. Aluminum coatings are particularly effective for containing and directing UVC and UVB radiation.

One commercial example of a device that can produce a very narrow beam of focused radiation from both diffuse and non-diffuse sources is the DLP (Digital Light Processing) projection technology originally developed at Texas Instruments, which requires very narrow, precisely controlled beams of light to project images on screens such as in a movie theater. This technology is said to be "light source agnostic" and can use a high-pressure xenon arc lamp generating diffuse light from a quartz arc tube or an LED, the light from which is shaped into a very narrow beam of focused radiation using mirrored surfaces and non-imaging optical devices. Lasers are also suitable light sources for the DLP technology without the need for collecting and shaping the light into a narrow beam. Thus, diffuse germicidal light sources can also be made into focused beams of germicidal radiation using means know in the art. If optics are employed for UV beam manipulation, fused quartz (a.k.a. fused silica) will be needed because of its high clarity and transparency to UV light, which is not the case with other glasses that can be used to manipulate visible light for example.

The emitter 20 may emit a relatively constant amount of germicidal radiation over a period of time. Alternatively, the emitter 20 may be pulsed to emit a relatively high level of radiation for a first-time period, followed by lower radiation or no radiation for a second time period. The pulsed bursts may emit more intense amounts of ultraviolet radiation than a continuous emission, but for a shorter duration. The length of the time periods may vary depending upon the desired extent of UV radiation that is to be emitted into the environment 100.

The emitter 20 may be a combination of multiple sources of germicidal radiation. This is advantageous because different wavelengths of germicidal radiation can cause different chemical reactions in the DNA of microorganisms, thereby achieving a higher probability of destroying the organism. Combining multiple sources of radiation into one is known in the art, even in the field of laser beam manipulation technology where very narrow beams of radiation from different sources are combined into one output beam, and these techniques can be used to combine multiple sources of germicidal energy into one focused beam of germicidal radiation.

Similarly, an emitter 20 can be combined with a visible light source to create a combined direction controlled beam of germicidal and visible light radiation if desired so that the beam of germicidal radiation and particularly the area at which it is being directed can be clearly seen to persons in the area. This feature can be used to visually confirm that the system 10 is working properly and the beam is not falling onto areas that are considered "unsafe" for germicidal radiation.

In one embodiment, the term "shape" of the germicidal radiation is used to indicate the cross-sectional contour or outline of the beam and includes the size of the cross-section. The cross section of the beam of germicidal radiation may be of various shapes and/or sizes, including a rounded outline, rectangular outline, or various other shapes. One embodiment is a rounded shape such as would be produced by a circular waveguide or opening. A rounded shape also lends itself more readily to the use of optics for beam shape manipulation, for example to make the beam wider or more narrow using beam expanders known in the art. The shape of the beam could be an irregular shape such as an "L" shape or a "U" shape, or it could be a hollow shape, for example a ring of radiation surrounding an inner core of no radiation.

The size of the focused beam of germicidal radiation leaving the emitter 20 could be of varying dimensions. Some specific embodiments include the beam dimensions ranging between 1 millimeter and 10 centimeters. The size of the beam may be dependent on the mechanism used to control the direction of the beam or in some embodiments the shape of the beam. In embodiments where galvanometers are used to control the direction of the beam, smaller beam dimensions will be preferred since the galvanometers undergo very rapid physical movement; the larger the dimensions of the beam, the larger the reflective surfaces of the galvanometers must be and therefore more difficult to control precisely. In other embodiments shutters or other radiation blocking shapes are put into the path of the beam to change its shape to prevent "unsafe" areas from being exposed to radiation while allowing some of the radiation of the beam to be emitted onto the "safe" areas; in such embodiments, a relatively large cross section of beam is desired so that parts of it can be more easily be blocked and the beam shape manipulated more easily (see FIG. 9 for an example of this embodiment).

An important feature of the beam is whether or not the sides of the beam are parallel or angled as it is emitted into the environment 100. If the sides of the beam are essentially parallel, like a laser beam, then the cross-sectional area of the beam is essentially constant as it travels (the diffusion is in most cases very small), and the radiation per unit area is essentially constant as it moves out from the emitter. The problem is that objects further away in the image will take more time for the beam to systematically move back and forth to fully decontaminate, such as a wall in the background. In other words, a beam size of 5 mm in diameter will look smaller from the perspective of the image on further away objects than closer objects in the image. For example, as one attempts to decontaminate the area of a room represented by an image, a beam with a fixed cross sectional area if shone into an environment back and forth as if to cover the entire area represented in the image, will cover four times the amount of area of the image as it passes over objects in front of a wall as it will when it passes over the wall in the background if the object is located halfway between the camera and the wall in the background.) The processing circuitry 51 can compensate for this if the engineering details of the radiation beam and diffusion are known. The other option is to use beams that have angular sides, such as would be created by a search light whose area when shown on objects some distance away can be much larger than the cross-sectional area of the source. If beams are used with angular sides, generated by optical and other devices known in the art, the further away the object, the more area the beam covers, but the lower the energy density, and the longer the beam will have to stay projected onto more distant objects to give the same amount of radiation as closer objects. Conversely, the time the beam shines on closer objects will have to be reduced to avoid over-exposing closer objects. All of these factors can be compensated for in the design, and these various design choices are envisioned in this application. Three-dimensional data of the environment and objects in the image will greatly help to ensure that the more distant "safe" areas represented in the image receive the proper amount of decontaminating radiation and closer objects in the "safe" areas do not receive too much. Capturing 3D (or three dimensional) data regarding the environment and objects in the environment can be very useful for the processing circuitry when determining how to decontaminate an environment using a radiation beam of parallel or angled sides.

The beam of germicidal radiation is controlled and directed into the environment by processing circuitry 51. The mechanisms for controlling the direction of the beam can include electromechanical means, piezoelectric and optical drives, and other beam positioning technologies. One embodiment is the use of laser scanners to control the direction of the beam of germicidal radiation. These scanners typically use galvanometers equipped with mirrors to control the direction of the beam, typically one galvanometer for controlling the X direction of the beam and another galvanometer for controlling the Y direction of the beam. These types of beam control mechanisms are commonly used to control the direction of laser beams in laser printers, laser projectors, medical equipment, and many other devices. Note: the term scanner or scanning is also used when describing the use of laser beams to scan objects and obtain distance or depth measurements to create 3D models of the environment or an object. Although depth measurement of the environment may be part of the camera system 30 as described elsewhere, the use of the term scanning here is a mechanism for controlling of the direction of the germicidal radiation beam. Other means to control the position of the beam include rotating mirror polygons as are employed in some bar code scanners and micro-mirrors mounted on semiconductor chips such as Digital Micromirror Devises or DMD's which are employed in some Digital Light Processing or DLP projectors. These devices are also capable of controlling the amount or intensity of radiation emitted by for example deflecting the radiation away from the exit of the emitter, thereby internally absorbing the deflected radiation, turning the source on and off. Any known method for manipulating the direction and intensity of a beam of radiation may be suitable for use in this invention.

Some systems, particularly those used in laser light shows, employ a combination of laser scanner technology and electromechanical technology to manipulate the direction of the beam. For example, LPS Lasersysteme is a company in Germany that makes laser scanners for laser light shows. One of LPS Lasersysteme's products is a "moving head laser projector LPS Impression Laser" in which a laser scanner is mounted in a disc-like housing that is mounted on a fixture that is capable of very rapidly rotating the scanner housing 360 degrees vertically while at the same time rapidly rotating the entire fixture 360 degrees horizontally. With a germicidal laser source replacing the light source in such a device, this type of direction control mechanism is capable of rapidly directing a germicidal beam of radiation from the fixture into the environment. If this fixture is then mounted on a device capable of physically moving it to other parts of the room, such as on a track or a self-propelled robot, then the environment can be more thoroughly decontaminated from many angles. Even without the scanning system, an emitter 20 could be mounted in the disk housing and the fixture that rotates the laser scanner could be used to direct the emitter 20, especially if that source has a low diffusion. FIGS. 6 through 9 show examples of such systems.

Figure 9:
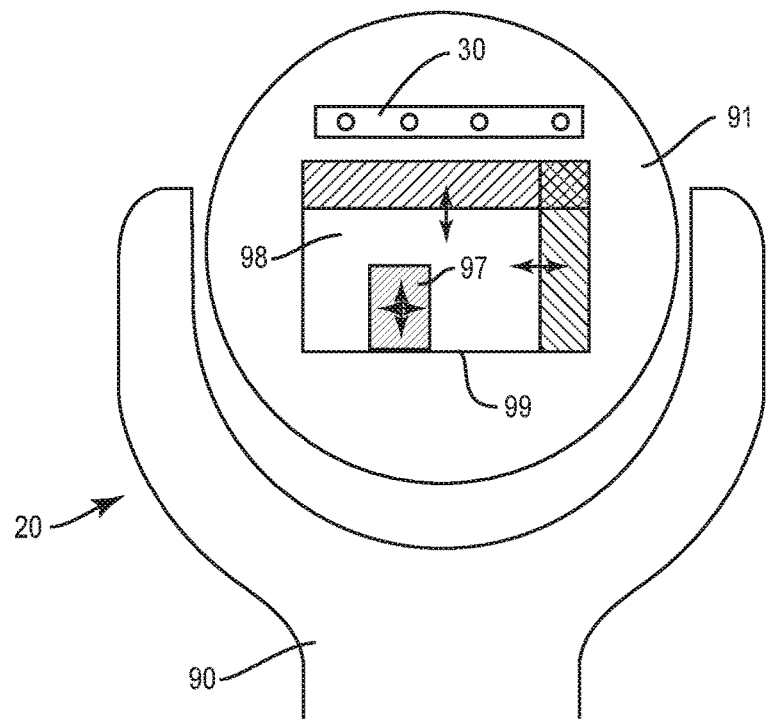
FIG. 9 is a perspective view of a germicidal radiation emitter.

Methods may also be employed to control the shape of the germicidal radiation beam. One such method is a simple shutter system mentioned previously. This can be a simple system that blocks certain parts of a germicidal beam being emitted into the environment. One envisioned embodiment of this method is a relatively large beam shape such as a 10 cm×5 cm rectangle emanating from the emitter 20 which when unobstructed can be projected onto an entire wall of the environment. If the control circuit detects "unsafe" areas representing exposed skin of persons entering the room or in the room, for instance, then the processing circuitry 51 closes certain shutters or mechanically or by other means puts radiation blocking objects into the path of the beam to block some or all of the radiation to prevent it from being emitted onto the "unsafe" areas. FIG. 9 shows an example of this embodiment.

Figure 4A:
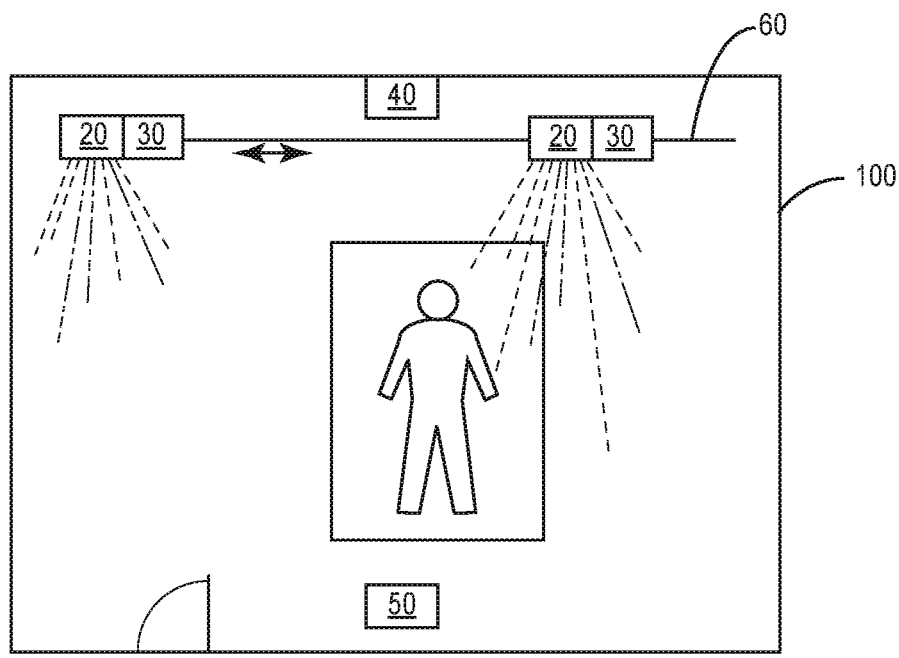
FIG. 4A is a schematic diagram of components of a system that are movable within an environment.
Figure 4B:
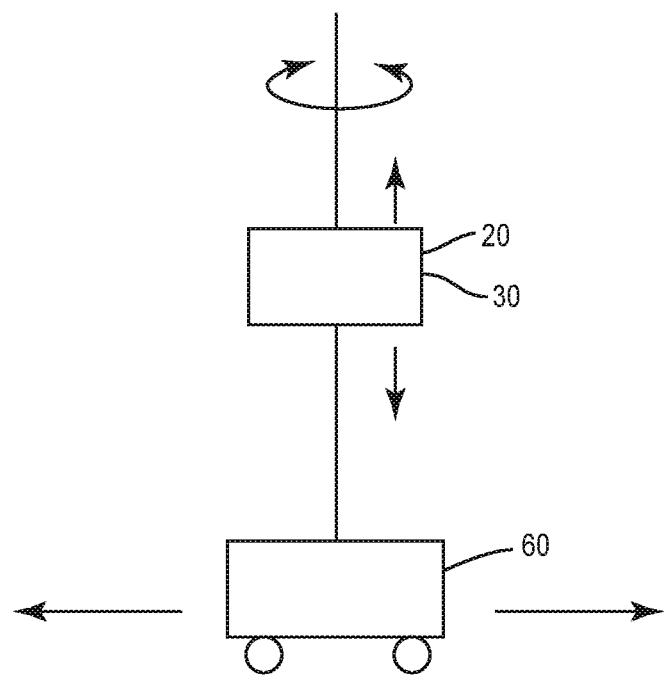
FIG. 4B is a schematic diagram of a device that moves the radiation emitter in the environment.

In another embodiment, the germicidal radiation emitter 20 is able to physically move to different locations within the environment 100. It is apparent that if the environment is being decontaminated based on images taken by imaging system 30, then system 30 should be located close to the emitter 20. In one embodiment, these components will be mounted close to one another and move together. The physical movement is automated and can be accomplished by the germicidal radiation emitter being mounted on a movement device 60 that creates physical movement of the emitter 20 within the environment 100. The movement device 60 that creates physical movement can be a motorized track or a pole to move the emitter 20 back and forth in a linear movement, as shown in FIG. 4A. The movement provides for the environment 100 to be decontaminated from more than one vantage point and more surfaces can be decontaminated quickly and easily. Any electromechanical means of creating physical movement can be considered for the movement device 60, including mounting the emitter 20 on a robotic vehicle or other device that is free to move throughout the room 100 as shown in FIG. 4B, in which the emitter is mounted on a pole which allows for 360 degree rotation and vertical movement. The floor plan could be programmed into the movement device 60, or it could have sensors that allow it to determine where in the room the obstacles are, technology similar to that employed in commercially available robotic floor cleaners.

Safe levels of UV radiation exposure have been calculated. In the United States, ACGIH has established a limit for exposure to UV radiation between 180 and 400 nm. The ACGIH threshold limit value (TLV) for UV is harmonized with the International Commission on Non-Ionizing Radiation Protection (ICNIRP) guidelines. Under these guidelines for broadband sources, the UV incident on the eye must be weighted by a relative spectral effectiveness function to obtain the "effective irradiance". The tabulated values for this weighting function can be found in the ACGIH TLV booklet or the ICNIRP guideline for UV. The integral of the effective irradiance over time (or, for constant irradiance, the product of effective irradiance and exposure time) shall not exceed 3 mJ/cm$^2$ in a day. If the effective irradiance varies over time, the 3 mJ/cm$^2$ limit should be applied to the effective radiant exposure, which can be measured using an integrating UV radiometer. The exposure limits may vary from country to country and should be reviewed for the standards that apply to each installation.

For the purposes of this application, "adequate" protection from germicidal radiation is defined as a level of protection that will protect a person in the environment such that they are not exposed to unsafe levels of germicidal radiation (i.e., levels of exposure that do not exceed government or medical allowed levels). For example, detecting whether or not UV eye protection being worn is "adequate" means in the United States that it is capable of blocking UV light such that the cumulative dose of UV light falling on the person's eyes does not exceed the threshold limit value for an 8 hour period.

The imaging system 30 for capturing images in the system 10 may include visible, infrared, and ultraviolet light cameras and possibly cameras that capture images using other wavelengths of electromagnetic energy. Imaging system 30 can include multiple cameras capturing images from the same or different wavelengths of the electromagnetic spectrum from essentially the same vantage point at essentially the same time, which is beneficial to aid in the computer analysis of the images when overlaying or comparing the information from the different images to one another by means known in the art. For example, visible light cameras can be used to capture images that are analyzed for skin color and body shapes (hands, arms, eyes, head, legs, etc.), and infrared cameras from the same vantage point can be used to capture images that are analyzed for the presence of heat or a higher temperature, possibly thus adding more confirmation to the program that it has indeed identified correctly a person's skin or body part. Infrared images are also beneficial in low lighting conditions where skin color analysis is more difficult or impossible, such as when persons in the environment are sleeping with the lights dimmed.

Taking images with multiple cameras from the same vantage point is helpful to minimize ambiguity in the analysis of the images. Commercially, multiple wavelength cameras for image analysis have been located within a few inches of one another, for example on laptops equipped with multiple cameras for facial recognition. Other commercially available camera systems locate multiple cameras three to six inches away from one another to get a three dimensional or stereo view of the environment. Some embodiments include multiple cameras located at the same or near location. Other embodiments may include multiple cameras that are spaced apart, which may be more applicable for use when objects are located farther away from the cameras.

The imaging system 30 may be equipped with wide angle or zoom or other specialty lenses. Video feed, or rapid succession of images taken of the environment, is also envisioned, as multiple images can make it easier for computer algorithms to detect persons in the environment (e.g. motion detection computer vision algorithms). For example, capturing multiple images of persons coming into a room may provide for clearer pictures of the persons. Additionally, these images may be used for additional image analysis, such as if the persons move around the environment, such as occurs when a person attends to the patient. This movement may make accurate image analysis more difficult. Drawing on the information captured when persons are clearly identifiable, such as when they first enter the environment, can improve computer image analysis in later time frames. Thus, continuous image capture at a rate of preferably multiple images or frames per second by each camera is envisioned as one embodiment. In one embodiment, it may be more beneficial from a safety standpoint to locate the camera system 30 close to the emitter 20, since safe decontamination using the directed beam is performed based on the perspective and information provided in the image. A location of the imaging system 30 within several inches of the emitter 20 is thought to be adequate and preferable for the purposes of this invention.

Imaging system 30 optionally includes a laser system for helping to determine the 3D location of objects and persons in the environment. This laser system is typically a safe infrared (IR) laser equipped with a scanning system or laser projector system which rapidly moves the infrared laser throughout the viewing field. When the reflected infrared laser light is viewed by an infrared camera, depth information for each pixel is obtained. Some commercially available camera systems have one IR laser scanner/projector and two IR cameras, with the two IR cameras located several inches apart to enable a stereo image of the environment to be obtained. Coupled with a visible light color camera, from essentially the same vantage point (e.g. between the two infrared cameras), a three-dimensional color image of the environment is obtained. The camera system just described is available from Intel under the tradename RealSense™ R200.

Another commercially available camera system also from Intel is the SR300 RealSense™ camera technology, which uses a combination of a color camera, an infrared camera, and an infrared laser to capture a three-dimensional video stream of the environment.

Another commercially available camera system suitable for camera system 30 is Apple's Primesense Carmine 1.09 camera system which features a variety of image capturing and tracking functions.

In this application, the safety of persons in the environment is of primary concern. A means of verifying that the output of the emitter 20 is not inadvertently falling on "unsafe" areas is to take images of the environment that captures the wavelengths being used for germicidal decontamination while the environment is be decontaminated. These images can be analyzed by processing circuitry 51 to ensure that the "safe" areas that are intended to be irradiated are indeed irradiated and the "unsafe" areas are not.

An ultraviolet light camera (if ultraviolet germicidal radiation is being used) feature could also be used to calibrate the system and direction control mechanisms of system 10. For example, the emitter 20 can be pointed to a safe area of the environment 100, such as a corner of a space or a ceiling. An image is taken of the safe area with the corner. The processing circuitry 51 could then direct the emitter 20 to emit radiation in the safe area. The UV camera captures where the beam actually hits the walls or ceiling, and makes adjustments accordingly. This process can be repeated until the processing circuitry 51 is able to direct the radiation beam to the place it intends with an acceptable level of precision. This process can be repeated for as many points throughout the environment as necessary until calibration is complete. The calibration can even be checked and adjusted as the environment is being decontaminated because at any given time the processing circuitry 51 knows where from the perspective of the image of the environment it is aiming the emitter 20, and an ultraviolet image of the environment 100 at that point in time will allow it to evaluate whether its aim is correct or not. Thus, the very nature of the system provides an opportunity for continuous, ongoing calibration of the direction control mechanism, provided that a camera is provided that can capture the wavelengths of germicidal radiation being emitted.

In some embodiments, imaging system 30 may not need to be co-located near the emitter 20. If the imaging system 30 or a combination of imaging system 30 and sensors 40 are located throughout the environment 100 and are equipped to determine the depth of the objects from each perspective, a three-dimensional model of the environment can be created which would enable the processing circuitry 51 to determine the appropriate path of the germicidal radiation from wherever the emitter 20 is located.

Figure 6:
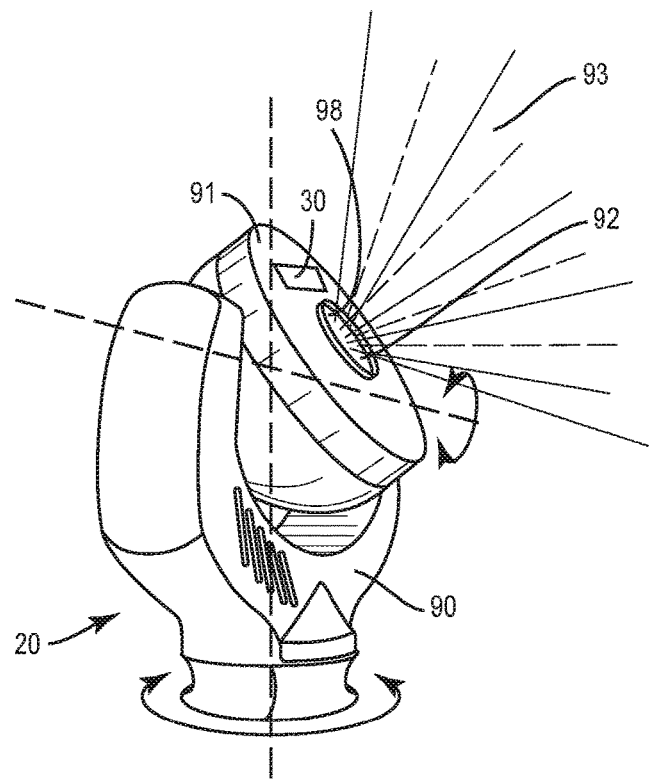
FIG. 6 is a perspective view of a germicidal radiation emitter.

The emitter 20 may include a variety of different aspects. FIG. 6 shows one embodiment of a direction controlled emitter 20. This direction control device is similar to the one commercially available from LPS-Lasersysteme particularly the moving head laser projector, hereafter referred to as moving head emitter 20. The emitter 20 includes a base 90 that supports a rotating disk 91 that includes the germicidal radiation source, such as a laser, LED, flash tube, etc. The base 90 is electromechanically controlled and able to rotate freely and rapidly around its vertical axis in either direction. The base 90 may be mounted at various orientations, or may be mounted on a robotic arm or other support that also can move within the environment. FIG. 6 illustrates an embodiment with the base 90 mounted on a horizontal surface in an upright position. The rotating disc 91 is electromechanically controlled and can be rotated freely and rapidly in either direction around its horizontal axis. The base 90 and the disc 91 together constitute a moving head. An imaging system 30 is mounted on the front of the rotating disc 91. The imaging system 30 may also be mounted at various other locations, including the base 90 and the back of the disc 91. The moving head emitter 20 includes a laser that is located inside the disc 91. The emitter 20 may also include a laser scanner 92 to control the output of the laser beam 93 as it is projected out into the environment 100. In this embodiment, the control of the direction of the radiation is provided by both the moving head 90 as well as the laser scanner 92, each of which are controlled by the processing circuitry 51. This embodiment provides some of the most precise control of the direction of the emitter 20 and may be useful in environments where there is a lot of activity and numerous persons moving about with unprotected skin exposed.

Figures 7A, 7B:
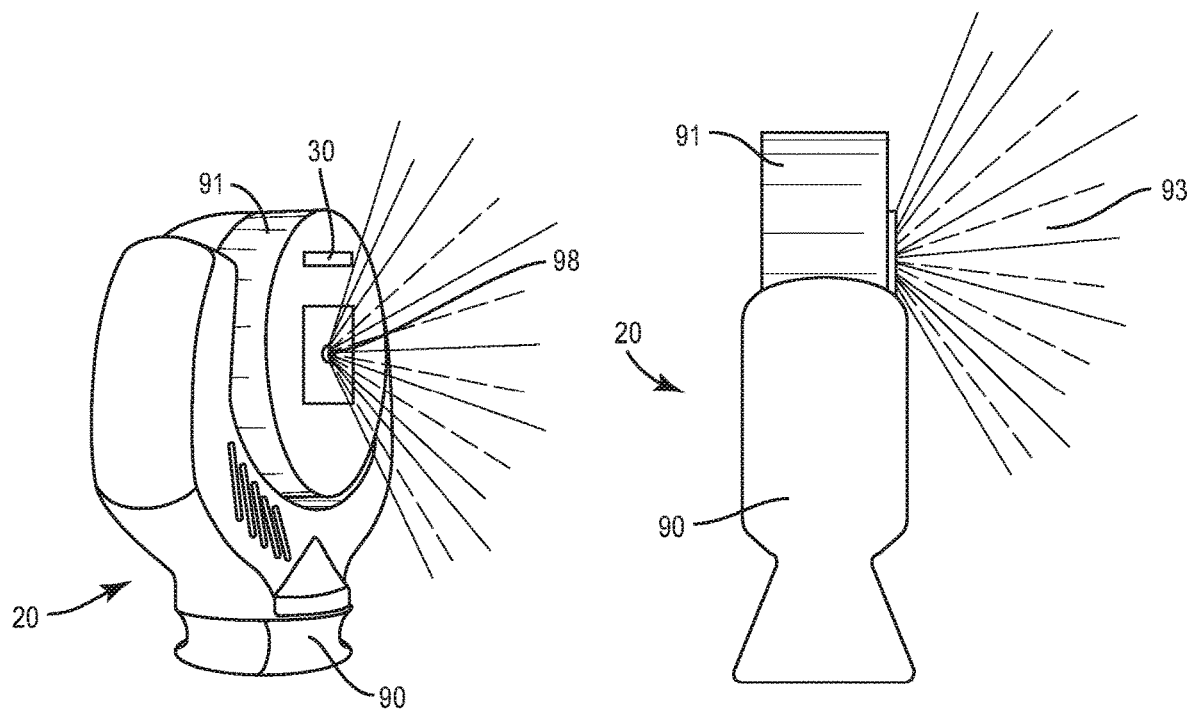
FIG. 7A is a perspective view of a germicidal radiation emitter.
FIG. 7B is a side view of the germicidal radiation emitter of FIG. 7A.

FIGS. 7A and 7B show a similar moving head emitter 20 that includes a source 98 such as an LED which is mounted flush with the face of the disc 91. The emitter 20 may also include or alternatively include a source 98 including an LED or a germicidal radiation lamp located inside the disc 91 with an opening or transparent window for the radiation to pass through. As illustrated in FIG. 7B, the radiation is emitted from this source in a hemispherical emission pattern and the edges of the germicidal radiation emissions are well defined. This design uses the moving head to control the direction of the hemispherical radiation output. Coupled with an imaging system 30 to monitor the presence of persons in the environment, the processing circuitry 51 could be configured to keep the beam directed onto areas in the environment where a hemispherical pattern would not come in contact with anyone in the environment or any unprotected skin of persons in the environment. This may be necessary since the beam is so broad it cannot be used for precise control, and since in some situations there may be few places in the environment 100 where such a large beam can be projected and still be kept away from "unsafe" areas.

In some embodiments, like those described in the previous example, if the beam area is too large to decontaminate "safe" areas of the environment as determined by the analysis of the image, the processing circuitry 51 may change the view or orientation of the imaging system 30 and emitter 20 until it finds an area in the environment 100 that can be decontaminated with the large beam. If it can find no such areas, it may turn the beam off until further images of the environment and analysis by the processing circuitry 51 enable the large beam to again be safely used in the environment 100.

Figure 8:
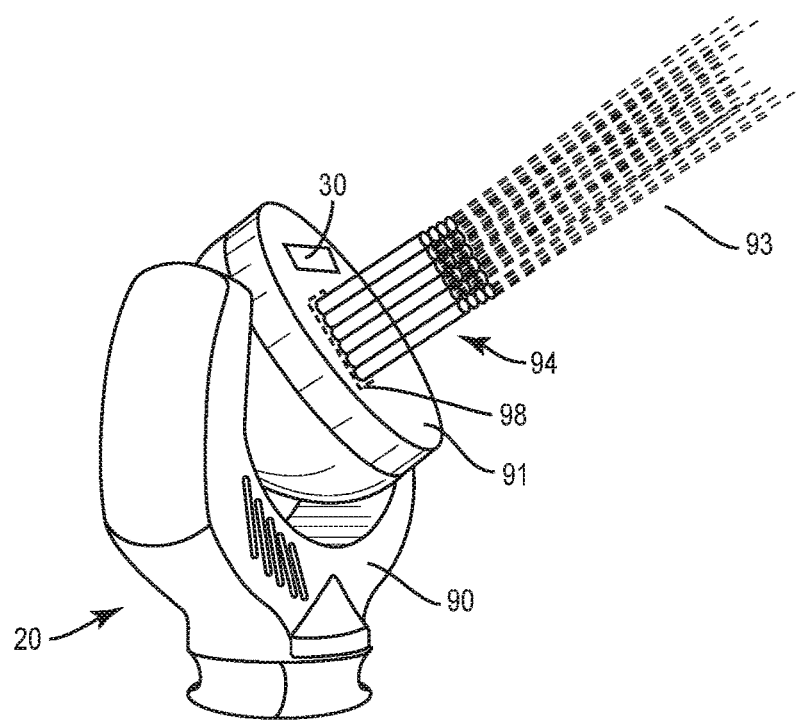
FIG. 8 is a perspective view of a germicidal radiation emitter.

FIG. 8 shows an embodiment that affords a beam area and degree of precision control in between the embodiments of FIGS. 6 and 7A and B. In this embodiment, waveguides 94 are provided to focus the output of the LED or other germicidal radiation source 98, mounted inside the disc 91, into a much smaller cross sectional area beam 93 than in FIGS. 7A and 7B, yet much larger than the cross-sectional area of the laser beam in the FIG. 6 embodiment. The waveguides 94 in FIG. 8 extend out of the face of the disc 91, although other embodiments may position the waveguides 94 inside the disc 91. The ratio of length to diameter of the straight and parallel waveguides 94 affects the diffusion of the focused beam of light. More waveguides 94 of smaller diameter can be compacted into an area to increase the length to width ratio, thus providing radiation output with less diffusion, without unduly extending the length of the waveguides 94. The waveguides 94 can be clustered in whatever shape is desired, whether square, round, rectangular, etc. In one embodiment, the waveguides 94 are clustered in a 4 inch square on the moving head and designed to have a low diffusion output that results in a roughly 4-5 inch square beam that is projected onto a wall ten meters away. Having a beam of known area and known diffusion can be input into the processing circuitry 51 in determining the preferred beam path for optimal safety and decontamination.

FIG. 9 shows yet another embodiment with a moving head design. In this embodiment, the radiation source 98 is located in or on the disc 91. A set of small diameter waveguides 94 (not shown) may guide the radiation and make it less diffuse. In this embodiment, a housing 99 is provided which contains shutters to block the radiation which move in the up and down direction and shutters to block the radiation which move in the side to side direction thus controlling the shape of the beam. Optionally, shapes 97 may be positioned in front of a portion of the beam to block certain portions of the radiation. A variety of different shapes and/or shutter designs may be used with the emitter 20. The housing 99 also provides a control mechanism to control the movements of the shutters and shapes. When the environment 100 is clear of persons or the processing circuitry 51 10 detects no persons or unprotected skin is located in the area of view as determined by image analysis, the shutters and shapes are moved out of the way and the environment 100 sees the full output of the area of the beam. If persons enter the area of view, the processing circuitry 51 analyzes where there are unprotected skin and body parts, and, according to the operational mode selected, moves the shutters and shapes to keep the persons in the field of view from being exposed to harmful germicidal radiation.

Figure 10:
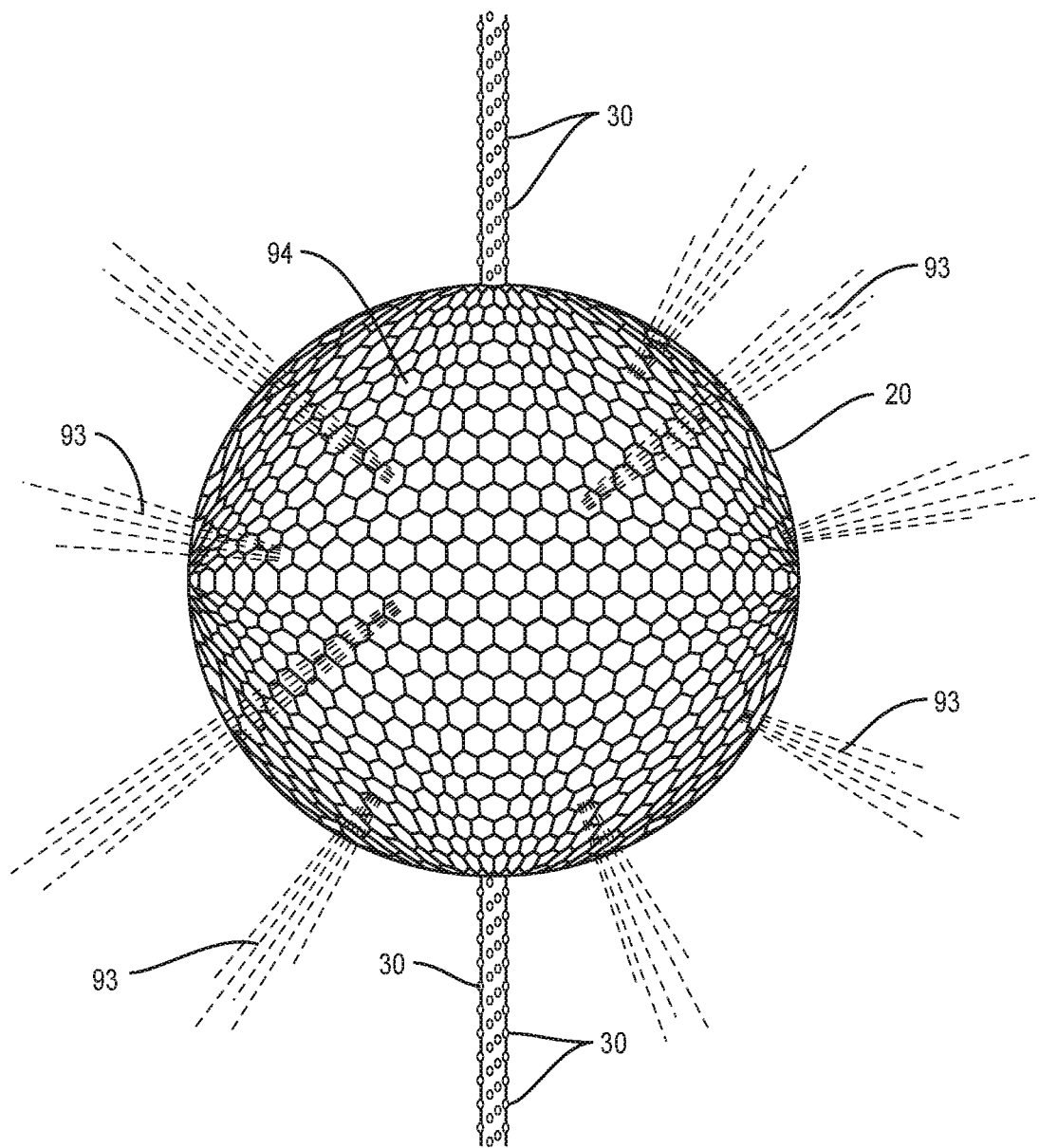
FIG. 10 is a perspective view of a germicidal radiation emitter.

FIG. 10 shows still another embodiment with the emitter 20 being a geodesic sphere made up of small waveguides 94 that are each shaped like a hexagon. Other embodiments may include the waveguides 94 having a triangular or circular shape. The design provides for the majority or entirety of the area around the sphere to be illumined with the radiation from at least one of the waveguides 94. In one embodiment, the emitter 20 is mounted on a shaft that can hang from the ceiling or be otherwise be supported. Cameras of the imaging system 30 are mounted into the shaft above and/or below the sphere and are designed to be able to capture a 360 view of the environment 100 without obstructing a waveguide opening. Germicidal radiation can be emitted from each waveguide 94, and the radiation from each waveguide 94 can be controlled individually. In this embodiment, each waveguide 94 has its own small LED light source 98 located inside the sphere at the base of each waveguide 94. In other embodiments, there is one light source such as a lamp at the center of the sphere from which each waveguide 94 gets its radiation, and each waveguide 94 has at its base inside the sphere a means of controlling whether or not light from the lamp enters that particular waveguide 94. In one embodiment, this includes a small cover that is either open or closed. The waveguides 94 in this embodiment have walls that are not parallel but are angled outward according to the arc of the waveguide so that the emitted radiation 93 will follow the angle of the waveguide 94 and spread out as it travels into the environment, thereby covering the entire room. In one embodiment, parallel sided waveguides 94 might produce points of radiation on the walls or objects in the environment 100 rather than allowing the radiation to spread out and cover the entire walls or objects as it travels various distances to objects in the room. An imaging system 30 captures images of the environment 100 that are then analyzed by the processing circuitry 51 for "safe" and "unsafe" areas for germicidal emissions. The processing circuitry 51 controls the direction of the germicidal radiation by determining which waveguides 94 to allow to emit radiation and which to prevent emission of radiation so that the "unsafe" areas do not get exposed to radiation and the "safe" areas are decontaminated. This system has the benefits of being a solid state system that has no moving parts and may be unobtrusive in its functioning, and a system that can simultaneously decontaminate in all directions.

Another variation on this design would be to mount the sphere on a track or robot for movement to various places in the environment 100. Rotating the sphere about its axis could also be easily done and may provide a more complete decontamination pattern if the radiation emitted from the waveguides 94 are found to give discontinuous spots on a wall rather than continuous coverage of radiation. The processing circuitry 51 may compensate for the changing orientation caused by rotation and control each waveguide 94 accordingly.

Another variation on the embodiment of FIG. 10 includes a flat panel design instead of a sphere with waveguides 94 similarly arranged next to each other and controlled. In one embodiment, this variation includes parallel-sided waveguides 94 and not angled waveguides 94. A flat panel design would not give 360-degree coverage but could be used for example as a full wall decontamination system that persons walk past or walk up to and turn around for decontamination of selected "safe" areas such as clothing or any areas that are not skin or eyes. The processing circuitry 51 continuously monitors their skin and eye locations multiple times per second as they stand there or walk past and only allows the small areas of radiation from the small waveguides to fall on "safe" areas.

After the imaging system 30 captures images of the environment 100, the processing circuitry 51 determines the location of exposed skin of persons in the environment and/or the positions of persons in the environment. Exposed skin is skin that is not covered by clothing, bedding, or other radiation-blocking materials worn or used as a covering by the user. Exposed skin is inadequately protected skin that could be exposed to harmful levels of radiation by the germicidal radiation if the image analysis algorithms and beam direction control algorithms fail to function properly to prevent such exposure. Additional information may also be obtained by analyzing the output of the imaging system 30, such as the location of persons within the environment, the number of persons in the environment, the position of the person in the environment and the location of their head, trunk, and limbs, etc.

The field of technology related to computer analysis of images is referred to as "computer vision" and is accomplished by various means. A variety of computer vision technologies are currently available, such as those available from Apple and Intel.

Computer vision technologies that are able to identify a person's skin in an image can be based on various image analysis techniques, including background removal (for images that have a known or controlled background), motion, color, or combinations of these. In embodiments where the environment is fixed and is not changing, the background is controlled therefore potentially simplifying the image analysis significantly so that the computer algorithms can focus on the things that are changing and unknown in the image, such as the persons entering and leaving the environment 100. The present application can also make full use of computer vision techniques that analyze for movement within the environment. This movement in the context of this application will be mainly persons that are moving therefore making the identification of persons and unprotected skin easier. Color analysis to detect skin in images is more difficult because lighting and skin coloration is difficult to control. Four known color spaces that are used for image skin color detection include RGB, YCbCr, HSI, and LAB.

Facial recognition is another useful sub-division of computer vision. Facial recognition technology is particularly applicable to clearly identify the eyes and location of the face of the persons in the image, thus helping to ensure that the location of the heads of persons in the environment 100. Facial recognition may also be useful in determining whether or not persons in the environment are wearing eye protection.

A computer vision software application to analyze the captured images may include Microsoft's Kinect which is a programming system that can be used to track persons in an environment. Kinect is typically used in conjunction with Apple's Primesense camera to capture images of persons in the environment for the purposes of gaming and remote control of devices based on body movements and voice commands. Using Kinect programming, maps of persons in the environment and their body movements can be created. Kinect could be useful in creating maps of the persons in the environment to better enable the processing circuitry 51 to identify "safe" and "unsafe" areas in the environment. A network of cameras (sensor 40) could be employed throughout the environment 100, especially in multi-room environments, to track each person's movements throughout the environment 100. Coupled with Kinect software tracking each person's movements, the system 10 or a network of systems 10 could be run more safely and efficiently because the movements of persons could be anticipated and the decontamination sequences run more thoroughly and safely. For example, if the system 10 is equipped with a network of cameras and the Kinect or other software tracking movements, the processing circuitry 51 could anticipate when a person might enter the field of view of an imaging system 30 and an emitter 20. When persons do enter the field of view, the processing circuitry 51 would already know how many persons there are and where their trunk, limbs, and head are located. Additionally, the processing circuitry 51 might change the field of view to purposely keep the person out of its field of view and decontamination area as long as possible to avoid possible "unsafe" areas in its field of view. Conversely, in embodiments where more direction-controlled decontamination of persons is desired, the information that a person is about to enter a room may cause the system to turn toward or focus more on fields of view that contain that person so that their clothing for example could be decontaminated. In other embodiments, continuous tracking of persons could be used to give more thorough decontamination to objects the person had just touched, such as door handles.

If needed to enhance the ability of the processing circuitry 51 to detect bare skin, a substance could be applied to the bare skin. This may include a powder or a liquid substance that dries and leaves a residue of some innocuous substance that is harmless to the person but which stands out prominently when viewed by the imaging system. This substance could be a colored or fluorescing dye or particle.

In some embodiments, "unsafe" areas may also be expanded by the processing circuitry 51 to include areas that contain radiation-sensitive items or items which for other reasons are not to be irradiated with germicidal radiation, such as medications or medical equipment. Likewise, some "safe" areas of persons or the environment for which exposure to radiation would not cause harm but is not desired, usually to provide a greater buffer zone around persons to make certain they are not exposed to radiation, can be designated "unsafe" areas if desired. The system can be programmed to identify other objects or areas to be avoided, or if they are in a fixed location, such as a mirror on the wall, that location can be programmed to be a permanent "unsafe" area to always be avoided when emitting germicidal radiation.

In one embodiment where there are fixed "unsafe" locations, a three-dimensional model of the room and location of the permanent "unsafe" locations is developed. The system may also be equipped with multiple sensors 40 on the doors to detect whether the door is open or closed. The system may also be equipped to determine by the analysis of the image whether the door in the image is open or closed. The system may be configured to consider an open door as an "unsafe" area to prevent radiation from being emitted from one room to another. The door would become a "safe" area again once it was determined from the sensors or image analysis to be in a closed position and could then be irradiated.

In other embodiments, objects in the environment 100 could be identified with ultraviolet, visible, or infrared markers that when an image of the object is taken show up clearly during the image analysis as being areas to avoid exposing to germicidal radiation. The markers may be specially colored tape or wrapping or tags that are put on the object. The marking method may include coating the object with a very thin coating of a fluorescent dye that is colorless to the eye but glows when exposed to UVA light. The imaging system can be provided with a harmless low power UVA light that it shines into the environment when it takes the image, and items coated with the fluorescent marker are clearly identified and determined by the algorithm to be "unsafe" areas for germicidal radiation exposure. In yet other embodiments similar to the one just described, the fluorescent, visible, infrared, or other marker could be added to a skin cream or lotion and applied to the skin to help the processing circuitry 51 identify areas of exposed skin that are "unsafe" and should be avoided. This lotion could also have germicidal additives along with the fluorescent or other marker to provide additional germ killing activity. In still other embodiments, special markers, such as a fluorescent additive or a colorant, could be added to garments. Having garments that stand out brightly in UV, visible, or infrared images can help identify where the persons in the environment 100 are located, they could help the processing circuitry 51 identify them as "unsafe" areas to avoid exposing to radiation, or just the opposite, the could be identified clearly as "safe" areas to expose to radiation in embodiments where decontamination of the clothing is desired and the system is equipped with enough precision of beam control to decontaminate the clothing and not the nearby and possibly unprotected hands and eyes. In yet another embodiment, in systems that are equipped to track each individual in the environment and uniquely identify each individual in the environment, the system can be programmed to treat certain individuals differently from others. For example, within a system that is programmed to designate clothing as a "safe" area for decontaminating in general, certain individuals can be designated by the system for no exposure anywhere on their persons, clothing or skin. In other situations, where each individual is tracked, certain individuals, perhaps those high-risk individuals who are highly susceptible to contagious diseases, or perhaps those individuals already infected with a highly contagious disease who are at high risk of infecting others, can be designated by the system to receive additional germicidal radiation exposure. Or perhaps these individuals marked for special treatment of their persons different from others in the environment could be given clothing with special markers that when processed by the image analysis algorithms clearly distinguish them from others in the environment and enable the system to treat them differently than other persons identified in the environment without those markers. Thus, this system is highly amenable to being tailored to many different decontamination scenarios and user needs.

The goal of the image analysis is to identify areas which are suitable for exposure to germicidal radiation and those areas which are not. This might be produced using a combination of any available computer vision technology. An accurate analysis of where in the environment the person or the exposed skin of a person in the environment is located is the primary output of this analysis. The identification of the head in either case is important because exposure of the head, specifically the eyes if not protected by eye protection, to a beam of germicidal radiation is highly undesirable.

In one embodiment, the images and other output from the imaging system 30 are analyzed for the location of persons in the environment and the location of their head, trunk, and limbs by a currently known method or program such as one or more of those already mentioned. A two-dimensional map is created from the perspective of the imaging system 30 that identifies where on that image of the environment the persons and their various body parts are located. The processing circuitry 51 is configured to run an algorithm that may identify areas where persons and their body parts are located and deem those areas to be "unsafe" areas for germicidal radiation exposure. This is a more conservative mode of operation and is intended to prevent any part of the person, whether fully clothed or showing exposed skin, to be irradiated with germicidal radiation. Any area not identified as "unsafe" on this two-dimensional map is considered "safe" for germicidal radiation exposure and is exposed to the beam in the decontamination step. In another embodiment, a three-dimensional image of the environment and persons in the environment can be obtained using the infrared laser scanning techniques. Again, in this embodiment, persons and their body parts are designated as "unsafe" for focused beam irradiation, but now additional depth information that will be useful in the decontamination step is also available. The disadvantage of these embodiments wherein the entirety of the person is designated "unsafe" and off-limits for germicidal radiation exposure is that no part of the person's clothing or other objects they might be carrying will be decontaminated by the germicidal radiation, and therefore some of the primary pathways of person-to-person transmission of disease are left untreated.

In another embodiment, the output from the imaging system 30 is analyzed for the location of exposed or unprotected skin on the persons in the environment and not necessarily the body position and limb positions of the persons in the environment. The numbers of persons and the location of the body parts of each person could also be used to help generate the desired information of the location of the exposed skin of persons in the environment, but the goal in this embodiment is to ultimately just determine where the exposed skin of all the persons in the environment from the field of view of the imaging system 30 is located. For example, the Kinect software might be used to identify persons and the location of their head, trunk, and limbs, so that other computer vision functionality capable of identifying exposed skin can more easily and with a higher probability know where to look in the image for exposed skin, such as the head/neck areas, arms/hand areas, and lower legs, etc. This information, as in the previous embodiment, is used to create a two-dimensional map or other suitable output from the perspective of the imaging system 30 that identifies where from that perspective the exposed skin of the persons in the environment is located, which the processing circuitry algorithm can deem to be "unsafe" areas for germicidal radiation exposure. This is a less conservative mode of operation compared to the embodiment where all parts of the persons in the environment are identified and considered "unsafe" for exposure. Any area not identified as "unsafe" on this two-dimensional map, that is areas where no unexposed skin was identified, are considered "safe" for germicidal radiation exposure, including clothing and objects the persons might be carrying such as clipboards, and are exposed to the beam in the decontamination step. In another version of this embodiment, a three-dimensional image of the environment and persons in the environment can be obtained using the infrared laser scanning techniques. The advantage of these embodiments where the exposed skin of persons in the field of view is designated "unsafe" and off-limits for germicidal radiation exposure, is that the person's clothing (e.g. lab coat, shoes, etc.) and other objects they might be carrying which could be heavily soiled with pathogenic microorganisms will be decontaminated by the germicidal radiation. If persons in the environment, particularly health care workers, are wearing gloves, and the gloves are of such a color that they are not identified by the computer vision as unprotected skin, then the gloves of the health care workers, which can be primary sources of person to person pathogen transmission, can be decontaminated in real time by the system 10, perhaps even while they are attending to the patient, using quantities of germicidal radiation that would be hazardous to the bare hands if the gloves were not being worn. This embodiment represents a major advance in decontamination technology with the ability to achieve real time and almost continuous decontamination of healthcare workers' and patients' clothing, gloved hands, bedding, instruments, and other objects in an environment.

In another embodiment, areas of persons that are determined by computer vision to be covered with clothing could be designated as "safe" areas for direction and intensity controlled germicidal radiation exposure. The clothing areas could be exposed to a lesser dose of radiation. In one embodiment, the dose is automatically controlled by the processing circuitry 51 controlling the speed and intensity of the emitted radiation as the beam passes over the areas of persons with clothing. In such embodiments, the output of the computer vision of the processing circuitry 51 would produce a two or three dimensional map of the image with three designated zones: "Safe" for higher amounts of radiation exposure, "safe" for lower amounts of radiation exposure, and "unsafe" for any radiation exposure. Even more gradations of energy and exposure are possible depending on the needs of the user and the ability of the computer vision algorithms to distinguish between different objects in the image. In some embodiments, "unsafe" areas such as unprotected skin and even the eyes may even be exposed to lower amounts of radiation, provided that the total amount of exposure does not exceed the safety limits for unprotected eyes or skin.

In some embodiments, the system is capable of operating in different modes at different times. For example, after a patient is discharged from a room, it is often desirable to do a more thorough decontamination before the next patient arrives. In such situations the system may be programmed to decontaminate in a different manner, such as using more intense radiation or longer exposure times or multiple passes over the same areas. Different modes can be preprogrammed into the system and selected by the user.

When analyzing the images and determining areas that are "safe" and "unsafe" for germicidal radiation exposure, the question will be raised about margin of safety. There are several things that will make the capturing and analysis of images and exposure of the "safe" areas with radiation less precise. For example, any blurring or distortion of the images will create imprecision, as will a lack of precise calibration of the image to the beam direction controller. Diffusion of the radiation is also a source of error, as has already been described. Movement of the persons in the image and the time lag between image capture, image analysis, and radiation exposure also create opportunities for error and inadvertent exposure of the eyes or exposed skin of persons in the image to hazardous germicidal radiation. Several things can be done in the image analysis step by the processing circuitry 51 to help account for these errors, the simplest of which is to leave extra room around the edges of the "unsafe" areas identified by the computer vision processing. This could be a buffer of a few centimeters to as much as a foot in cases of higher uncertainty. Another way of reducing errors is in the rapidity or frequency at which the system captures and analyzes images of the environment and completes the decontamination cycle. Cycle frequencies of multiple times per second are envisioned for all of these steps and are within the capabilities of current technology. Regular calibration of the beam direction controller relative to the images being captured will also help reduce error, as has already been described.

Figure 11:
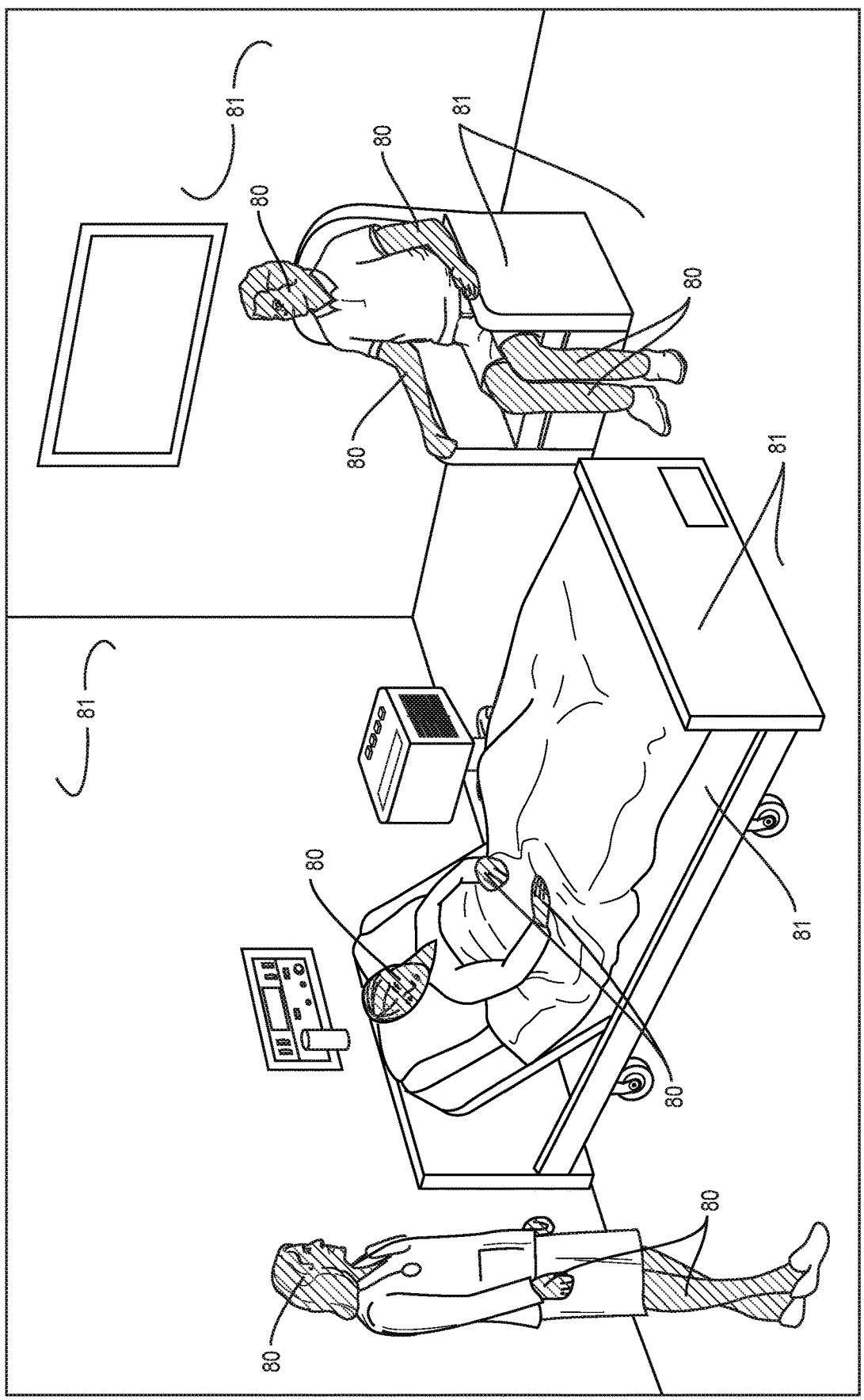
FIG. 11 is a perspective view of an image of an environment that is being analyzed by the system.

FIGS. 11 through 15 illustrate aspects of the image analysis and decontamination sequence. FIG. 11 shows an image of a room with persons present where the computer vision algorithms run by the processing circuitry 51 have identified the exposed skin of persons in the image and designated these as "unsafe" areas 80 for germicidal radiation exposure. Any area not designated as an "unsafe" area in the image is considered a "safe" area 81 for germicidal radiation exposure.

Figure 12:
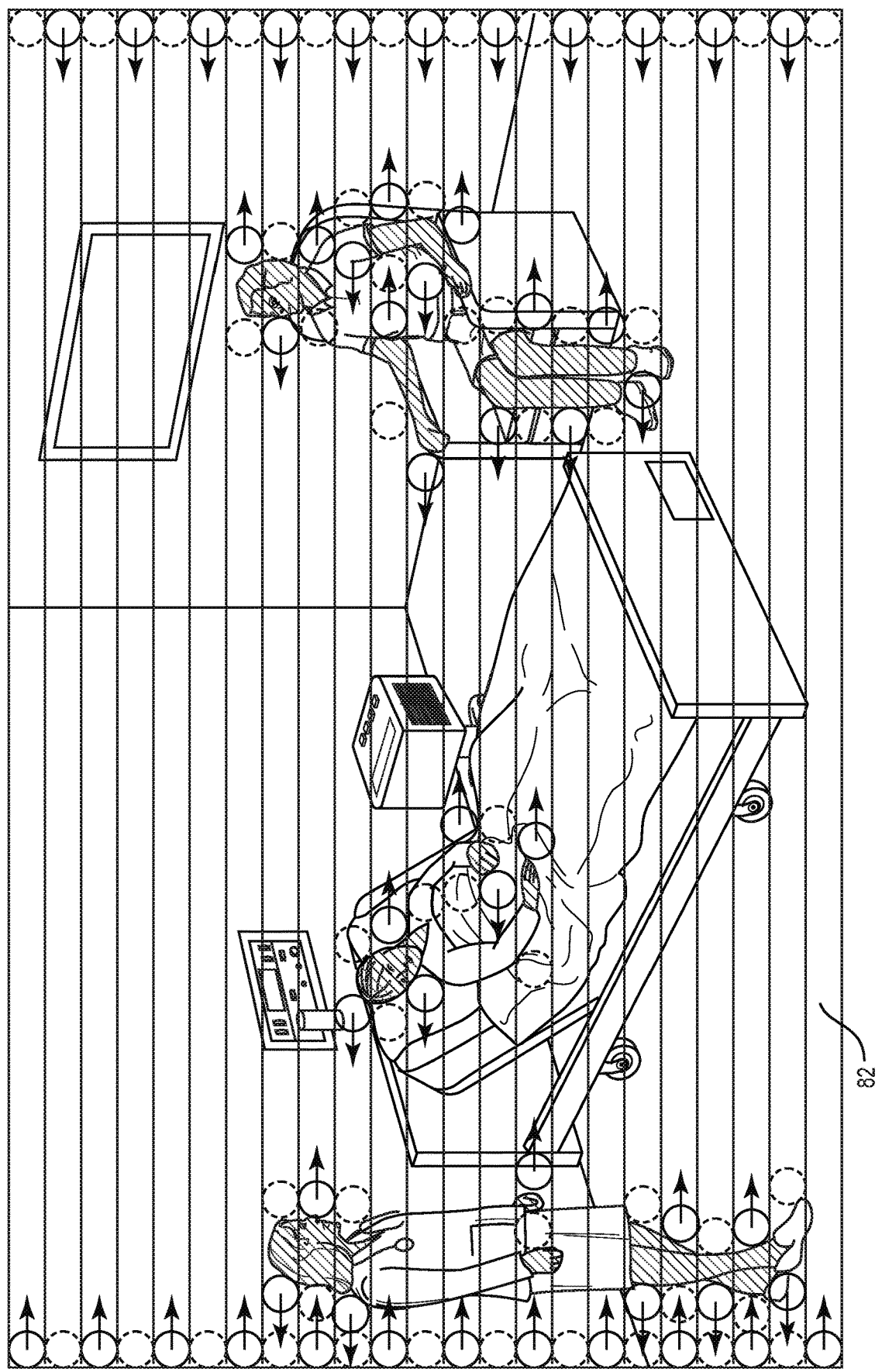
FIG. 12 is a perspective view of an image of an environment that is being analyzed by the system.

FIG. 12 shows the same image as FIG. 11 where the processing circuitry 51 has identified a pathway 82 for decontaminating the environment with direction controlled germicidal radiation of a circular beam of about 4-6 inches in diameter. In this embodiment, only exposed skin is considered "unsafe", and persons' clothing is considered "safe" and is able to be decontaminated by the radiation beam. In this example, the beam moves back and forth from one side of the image to the other in a systematic manner, starting at one side and sweeping from side to side, stopping at either an "unsafe" area or the other side of the image. The radiation turns on at the start of the "line" and is turned off when the "unsafe" area or border is reached. The processing circuitry 51 then repositions the emitter 20 on the other side of the "unsafe" area or moves it to a new line and continues the sweep across the image. Many different movement patterns and functionality could be chosen. Although not every square inch of "safe" areas are exposed because of the size limitations of the beam, the pathway is chosen to maximize efficiency of movement and ensure that none of the "unsafe" areas receive any germicidal radiation. In this embodiment, the beam cross sectional area expands into the environment so that the image area that it covers as it passes over nearer and farther objects from the perspective of the image is relatively constant. If the processing circuitry 51 is programmed to administer the same dose of radiation to every area toward which it is directed, then the beam must slow down for further away surfaces due to the fact that the expanding beam has a lower energy per unit area on further away objects than it does on closer objects. Slowing down or multiple passes over further away areas would be necessary to compensate for this. In other embodiments, a steady-rate sweep of the area may be sufficient, especially if the decontamination is being repeated over and over.

Figure 13:
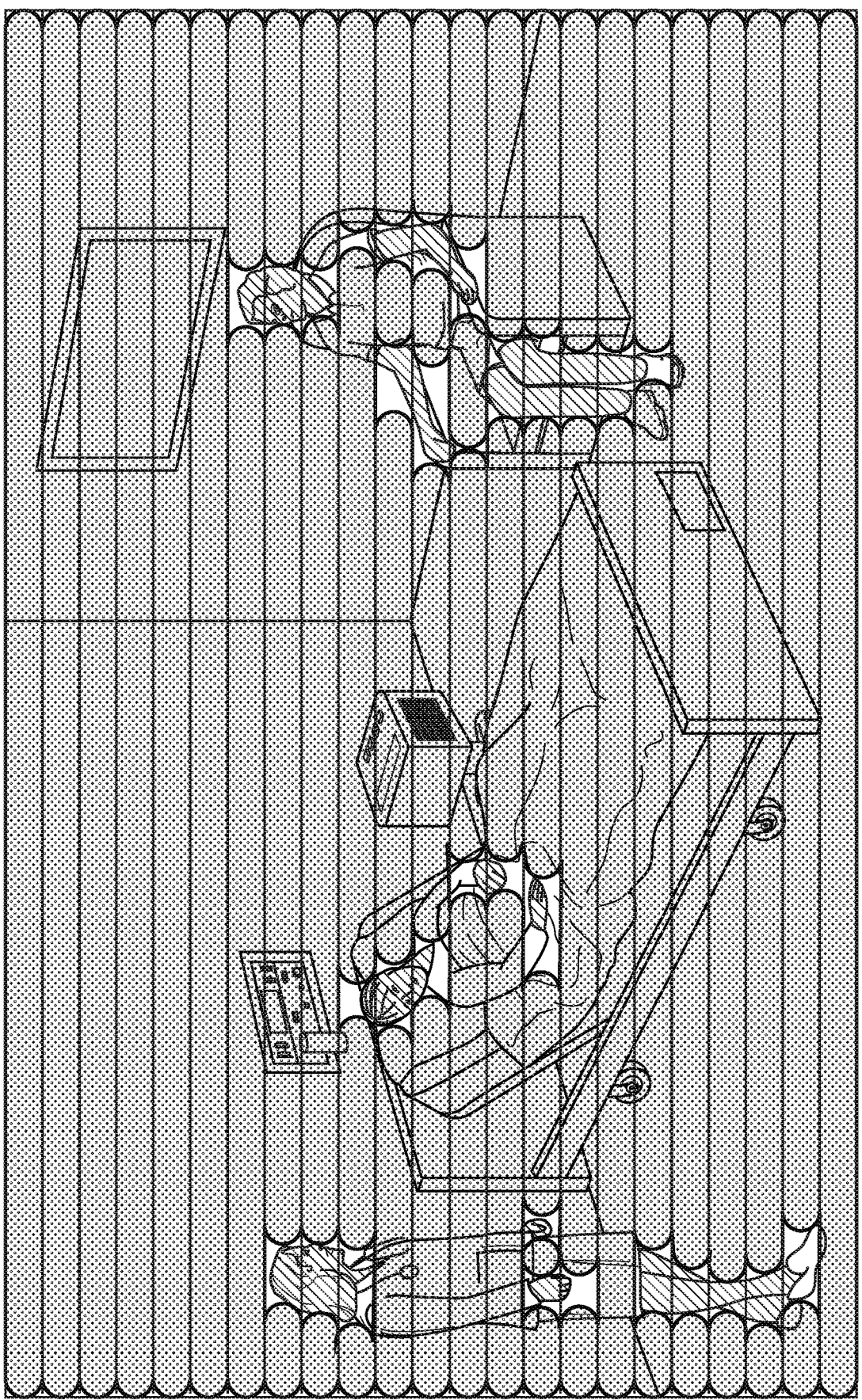
FIG. 13 is a perspective view of an image of an environment that is being decontaminated by the system.

FIG. 13 shows the areas of the environment from the perspective of the image that have been decontaminated by the beam. Persons are often in motion, so the entire radiation sequence may be very rapid and faster than the movements of individuals. This is why laser projector and similar technologies using scanning galvanometers can be useful in this application because the control of these beams of radiation is very precise and the movement of the beam can be very rapid. FIG. 13 also shows what an exposure of an image taken in the germicidal wavelengths used for decontamination might look like if the camera "shutter" was kept open throughout the decontamination cycle of that single image. The areas exposed to the germicidal radiation would show up in contrast (darker or lighter) than the areas that did not receive direct exposure to the radiation. This type of image could be stored after every cycle to show that persons were not exposed to the radiation, or if they inadvertently were exposed, information as to where on their body they were exposed. Additionally, the length of exposure could be determined. This image could also be used as an aid to quality control.

Figure 14:
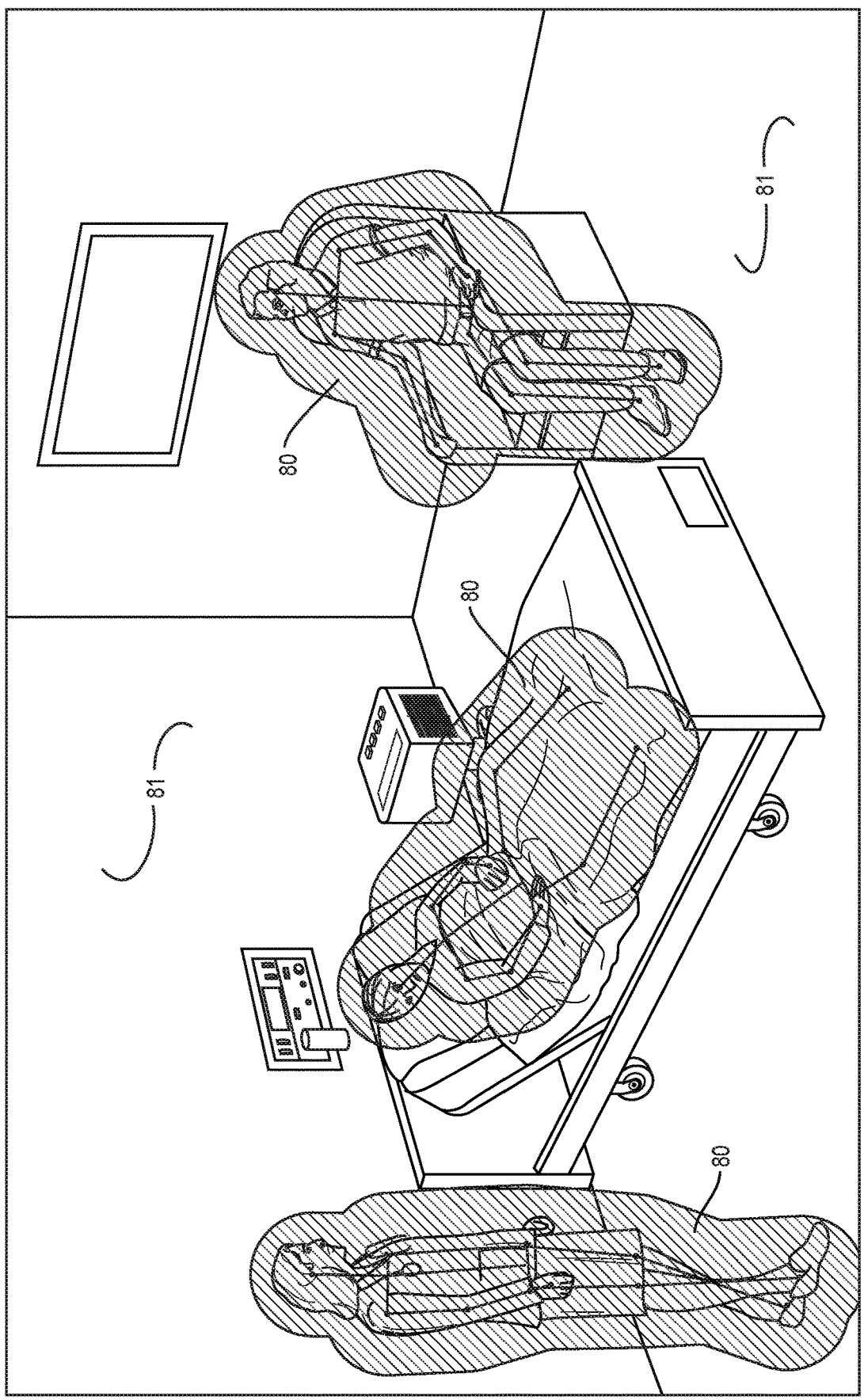
FIG. 14 is a perspective view of an image of an environment that is being analyzed by the system.

FIG. 14 shows the same image analyzed in a different manner. In this embodiment, it is desired that no part of any person, whether exposed skin or clothing, be exposed to germicidal radiation. In addition, it is desired that at least a 6 inch buffer or more be provided around the outline of each person. Also in this embodiment, additional sensors 40 area provided in the environment to allow full person tracking and continuous body position monitoring, which the processing circuitry may see as stick figures or skeletal outlines showing the approximate positions of the person's body and limbs. This can aid the processing circuitry in determining where the "unsafe" areas which in this case are entire persons and areas around them. Notice that compared to the analysis in FIG. 11 of exposed skin as designated "unsafe" areas, the amount of area of the image that is "safe" for decontamination 81 in FIG. 14 is significantly less than the "safe" areas of FIG. 11.

Figure 15:
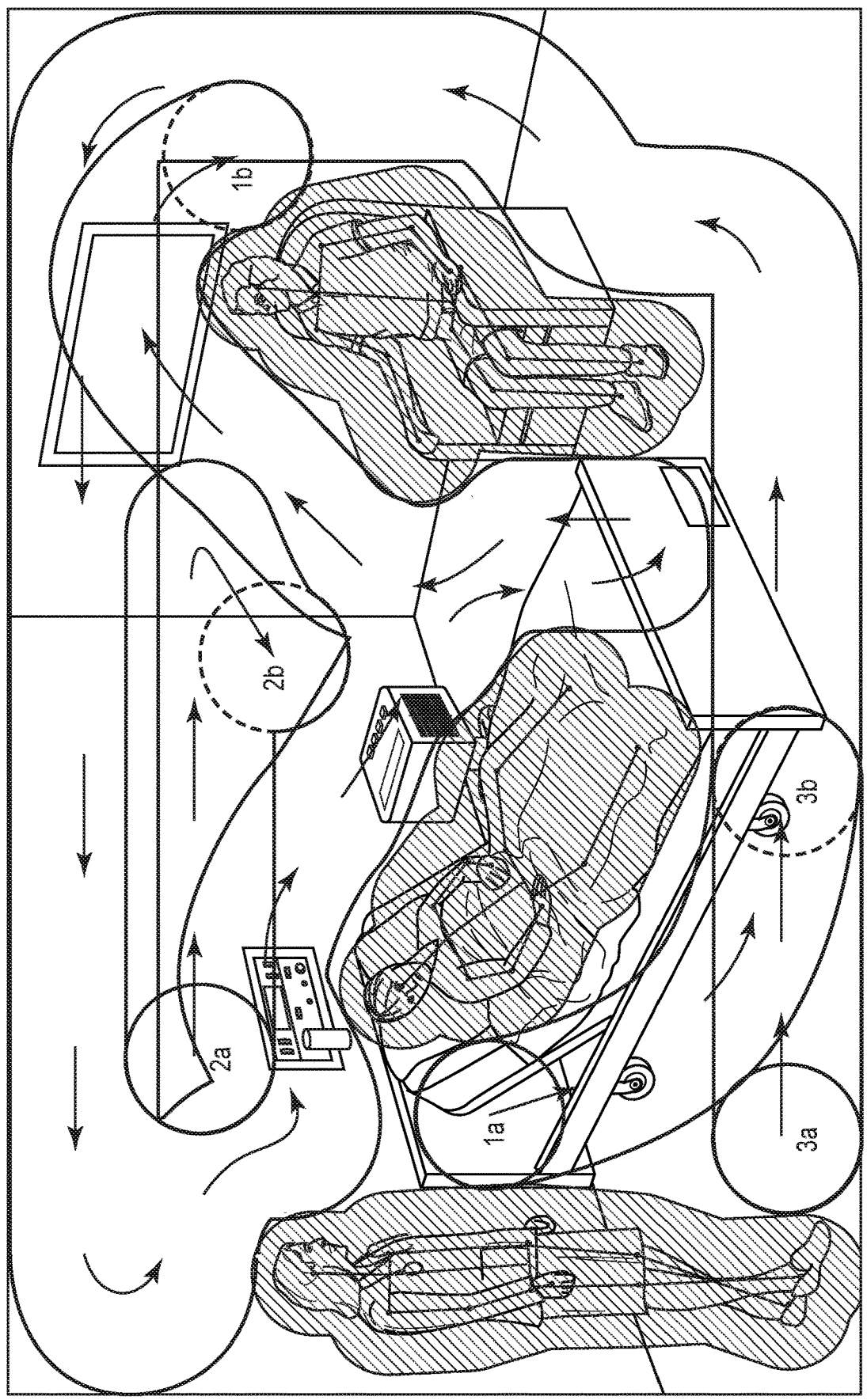
FIG. 15 is a perspective view of an image of an environment that is being analyzed by the system.

FIG. 15 shows the path that the processing circuitry 51 might choose for decontaminating the image of FIG. 14 and its "safe" areas 81. In this embodiment, the beam diameter is significantly larger than in FIG. 12. Instead of moving back and forth across the image, the decontamination path is moved more freely in the most efficient manner determined by the processing circuitry 51. In this example, the majority of the decontamination is completed in one continuous sweep (from location 1a to location 1b) and is completed by two additional much shorter paths (from location 2a to 2b and 3a to 3b). Notice that in this embodiment with the larger area beam width, there are more areas in the image that are not able to be decontaminated due to the beam size. In one embodiment, the beam does not extend outside the image because the processing circuitry 51 does not know what is beyond the borders of the image and has to consider the area beyond the image as "unsafe" for germicidal radiation exposure.

The system 10 may be equipped with one or more sensors 40 to detect the presence and/or location of persons in the environment and/or whether eye protection is being worn by persons in the environment and/or whether protective coatings on the skin are being worn. Sensor 40 can be a single sensor, a camera, or multiple sensors or multiple cameras. The processing circuitry 51 is configured to receive signals from sensor 40 and operate the emitter 20 in a way to decontaminate the environment while keeping persons in the environment safe.

The system 10 may be configured with one or more sensors 40 to detect the presence and position of the person in the environment. When multiple sensors 40 are used, the sensors 40 may be the same or different. The system may include multiple sensors and/or multiple wireless technologies to triangulate the position of individuals, which is needed for more accurate position measurements.

For tracking at least one of the presence, location, or position of persons in the environment, the sensors 40 may include various types of sensing technology, including but not limited to motion or movement sensing, image capture and video monitoring, RFID's, thermal or infrared sensing and imaging, microphones, sonic or ultrasonic transducers, lasers, light-emitting diodes (LEDs), photodetectors, and photoresistors. This may include sensor 40 on the doors within the environment that can detect opening/closing. Input devices 59, such as card readers, keyboards, etc. may also be located about the environment. The system 10 may include input devices 59 for persons that enter the environment to input information such as a passcode or card swipe in order to enter the environment 100, or sections 110 of the environment 100.

The sensor 40 may also be an RFID tracking system where tags are assigned to the person, such as tags incorporated into a wrist band. RFID readers 40 are positioned in the environment 100 to read the electronic information stored on the tag to determine the location of the person in the environment. The processing circuitry 51 may identify and/or monitor persons in the area by wrist or ankle bands, lanyards, or any other means to attach a transmitting or other location detecting device to a person. Location monitoring may also be achieved by assigning eye protection or other PPE to persons entering the area wherein a locating device is embedded in the eye protection or PPE. For example, a location detection transmitter could be installed in a pair of germicidal radiation safety glasses or other eye protecting device, or a location detection transmitter could be installed in an obscure part of a germicidal radiation protecting over-garment, such as a smock or light coveralls. Also, combinations of systems could be used.

In one embodiment, a network of video monitoring cameras 40 coupled with a computer vision software application such as Microsoft's Kinect, may be useful to track persons in an environment. Kinect is typically used in conjunction with Apple's Primesense camera to capture images of persons in the environment. Using Kinect programming, real time tracking of persons in the environment and their body movements is possible.

Detecting a person in the environment 100 may also occur when the person first enters. The processing circuitry 51 may require that the person pass through a particular location which is equipped with a sensor 40 to detect the person. In one embodiment, entrances into the environment 100 are kept locked and require user input through an input device 59 prior to admission. This may include a user swiping an ID card through a card reader, or entering a code into an input device 59. FIG. 1 includes this concept with a card reader 59 positioned at the door of the environment 100. This user input may be passive, such as the user walking within proximity of a sensor 40, or the person being given an RFID or like device that is read to signal entry.

The processing circuitry 51 may be configured to receive signals from one or more of the sensors 40 to determine the number of people within the environment. Based on this information, the processing circuitry 51 may adjust the germicidal radiation emitted into the environment in relation to the number of persons, either by increasing or decreasing the amount of radiation emitted with more persons in the environment.

Similarly, the processing circuitry 51 may receive signals from one or more of the sensors 40 to detect motion of the one or more people in the environment. Germicidal radiation may be increased during times of higher activity such as coughing or walking around and may be decreased during times of lower activity such as sleeping or watching television.

The system 10 also includes one or more sensors 40 for detecting that eye protection is being used by each of the persons in the environment 100. These sensors 40 may be on the eye protection or may be positioned away from the eye protection.

Various types of germicidal radiation eye protection can be used with the system. Examples include glasses (preferably with side shields or wrap-around style), goggles, face shields, a full helmet, or any device worn on the head that can protect the eyes from harmful germicidal radiation. Polycarbonate lenses are often used for blocking UV light, since additives (dyes) can be added to give 99.9% blockage of UV between 180 and 400 nm (this range encompasses UVA, UVB, and UVC); various types of UV-blocking eye protection are commercially available. Eye protection that shields against HINS light can include eye protection made of materials transparent to longer wavelengths of visible light but which block violet and blue wavelengths, which is commercially available. This eye protection would be for use for patients, health care workers (HCW's), visitors, factory workers, office workers, and anyone in an area of germicidal radiation exposure.

Eye protection that is worn by the user may be detected in different manners. In one embodiment, each person that enters the environment 100 is equipped with a communication unit. The unit includes control circuitry that includes one or more programmable processors and associated control software. The communication unit also includes one or more receivers or transceivers, such as one or more RFID signal receivers, RF transceivers of various types which could include cellular-type interfaces all without limitation. The RFID signal receivers can receive information from identifiers, such as RFID sensors, or tags, which are associated with the eye protection that is worn by the person. The communication unit periodically polls for the existence of the identifiers. If the unit does not receive a signal from the identifier, the unit communicates with the processing circuitry 51 thus indicating that the eye protection is not being worn.

The eye protection may be equipped with switches and/or sensors and the like that detect the location of the eye protection and whether or not it is positioned in a way that signifies whether or not the user is adequately protected. When the eye protection is in the proper location on the user, the switches or sensors are activated indicating proper use to protect the user. When the eye protection is improperly positioned or not in use, the switch(s) and/or sensors remain open or closed or in an "unsatisfied" condition or state that indicates the eye protection is not properly positioned. The processing circuitry 51 monitors the switches and/or sensors to determine use of the eye protection. For example, small, unobtrusive switches or sensors located in the eye protection nose pieces, bridge, frame, strap, etc., could detect whether or not the eye protection is properly fitted on the head. In the case of protective glasses, small switches or pressure sensors could be mounted in the nose piece and behind the head in an elastic strap. When the eye protection is in position and held in place with tension on the strap, both front and rear switches or sensors detect pressure, and these in turn communicate through a wireless transmitter (or a physical wire for persons that are relatively immobile) in the eye protection to the processing circuitry 51 indicating proper donning of the eye protection. Similarly, pressure sensors may be included on a strap used to secure the protective equipment to the person. If the pressure sensed is below a predetermined amount, the processing circuitry 51 interprets that the equipment is not being worn properly.

Pressure sensors could be mounted around a head band (like a hard hat type head strap) that would sense pressure against the head. Once the sensors detect a certain amount of pressure in certain areas, the PPE is equipped with a wireless transmitter to send a wireless signal to the controller that allows the germicidal radiation emitter to turn on. If the pressure sensors detect loss of pressure (in the event the headpiece comes off, for example), then a wireless signal is sent which would cause the processing circuitry 51 to deactivate the emitters 20. In the case of eyeglasses, pressure sensors could be located in the nose pads of the glasses and optionally on the ear pieces to sense when the glasses are properly positioned on the face.

Temperature sensors, touch sensors, humidity sensors, etc., may also be useful to determine whether or not the PPE is being worn correctly. For example, a temperature sensor in the nose pad or other location would indicate that it is being worn against the skin, and a humidity sensor may pick up humidity from the skin. Current or conductivity sensors (contact with skin completes microcurrent circuit and indicates the eye protection is on), proximity sensors, infrared sensors, ambient light sensors (or lack thereof if the nose piece is against the nose), position sensors, color sensors, any of these and many other sensors could also be useful in determining whether or not eye protection has been donned properly.

Other ways to detect the use of this type of protective eye protection include visual monitoring systems coupled with computer analyses of the images. For example, facial recognition software and the like can be used to monitor faces of persons in the area to determine whether the eye protection is being worn properly.

To ensure adequacy of protection, germicidal radiation sensors 40 can be positioned near the eye and on the inner side of the lens(es) to monitor germicidal radiation getting through the eye protection. This germicidal radiation sensor can record on a continuous basis the germicidal radiation on the inner side of the lens or could be set to be triggered only if the radiation exceeded a certain amount. This sensor could communicate with the processing circuitry 51 or simply record the information for future use. If the eye protection comes off the face and germicidal radiation is present in the environment, the sensor detects the germicidal radiation and sends a signal to the controller so appropriate action can be taken to decrease the emitters into a safer mode of operation, including turning the emitters off. This sensor could be the primary sensor 40 to determine whether or not the eye protection has been properly donned or could supplement other sensors 40 that determine whether the eye protection has been properly donned. Data from this sensor could be very useful to quality control and confirming that the system is working properly or can be stored and checked if anyone complains of eye problems after using the system.

Sensors 40 may also be configured to detect for skin protection on the person. Previous descriptions described methods for detecting the presence of exposed skin on persons in the environment using computer analysis of images and the input of other sensing devices. Methods for detecting protected skin build on those systems and methods. Protected skin is defined as skin that is not covered by clothing or other radiation blocking materials but rather is protected from germicidal radiation by creams, lotions, or other coatings that contain substances to block some or all of germicidal radiation, referred to hereafter as "protective coating," applied to the skin. Ultraviolet radiation blocking sun tan lotion is an example of a protective coating useful in this application.

Most embodiments of skin protection in this application involve adding an ingredient to the protective coating that is detectable by the imaging system 30 or sensors 40. For example, the protective coating may include colorants, such as white or blue, that allows the computer vision to differentiate between unprotected skin and skin that has protective coating applied. The protective coating may include ingredients that are not visible to the eye but are highly visible to a camera at some non-visible light wavelength, such as a fluorescent additive or dye that is invisible to the human eye but which cause skin with the protective coating to have a different visual appearance when viewed by an ultraviolet camera. If the substance requires other wavelengths of radiation to be emitted to activate the substance so it can be detected, such as a black light emitting harmless levels of UVA radiation onto fluorescing additives, for example, the invention provides this as well.

The detected information from imaging system 30 and sensors 40 is sent to the processing circuitry 51 that processes the data and is able to differentiate bare skin (i.e., unprotected skin) from that with protective coatings or other protection (e.g., clothing). The processing circuitry is then programmed to allow direction controlled beams of germicidal radiation to be directed onto the protected areas of skin but not on unprotected areas of skin. With this feature of the providing for the analysis of protective coatings on the skin, a deeper degree of decontamination is possible of not just the environment and in some cases the clothing of persons in the environment, but also of the skin of persons in the environment.

In one embodiment, a local viewing device is provided that displays the output of the computer vision protective coating analysis. In this embodiment, the nurse or patient applies the protective coating then views the skin on the local viewing device, such as a monitor or possibly even a hand held device such as an iPad, where a computer-enhanced image is displayed that shows areas of the skin that have been covered with the skin protection and those areas of skin that have not. Cameras or sensors 40 could even be built in to a local hand-held viewing device for close up viewing and analysis of unprotected skin areas. The protective coatings can then be reapplied as needed, and the process can then be repeated until the desired result of complete coverage is obtained.

In another embodiment, biocidal substances are added to the protective coatings to kill more microorganisms. This combination of UV radiation plus biocidal skin coatings can greatly enhance the destruction of microorganisms in the immediate environment of persons and on the persons themselves, something no other system is able to provide on a continuous basis.

The processing circuitry 51 may also be configured to determine intermediate degrees of protection. For example, the processing circuitry 51 may detect an amount of protective coating that is applied on the skin that indicates an intermediate level of protection. The processing circuitry 51 may then operate in one of the modes that is applicable to the extent of protection that is detected.

The protective coating applied to a person may have germicidal activity from either the use of organic or inorganic chemicals added to the cream or the use of nanoparticles of $TiO_2$ or other particles that have germicidal activity in the presence of germicidal radiation. Nano sized $TiO_2$ particles have a catalytic effect to destroy microbes when light hits the particles.

In one embodiment, the system 10 includes one or more infrared or heat sensing cameras to detect areas of a patient's skin that get too warm when exposed to germicidal radiation. The elevated temperature may indicate that the skin is not protected adequately. Upon the detection of the elevated temperature, the processing circuitry 51 can either stop the emitters 20 or reduce the amount of germicidal radiation. The processing circuitry 51 may also be configured to cause a signal to be sent to a remote party (e.g., nurse) who can then more closely evaluate the situation and make certain that the protective coatings are applied.

The protective coatings may use both coalescing polymer films (lattices) as well as non-coalescing coatings such as creams or lotions. In the case of the latex polymer films, the formulation includes pigments and additives to block UV radiation, for example, and optionally provide germicidal benefits. An advantage of a latex film would be a protective layer that is more durable and does not rub off as easily as the patient moves about. If polymers are chosen that inherently block UV light, a thin polymer skin layer may adequately protect persons in the environment and have a variety of advantages.

In one embodiment, small, smart, germicidal radiation sensors and transmitters could be attached to the skin in various places (back of hand, neck, arms, etc.), and if ever these sensors detected germicidal radiation above certain levels, the processing circuitry 51 could cut back on the radiation or take other appropriate action.

Figure 5A:
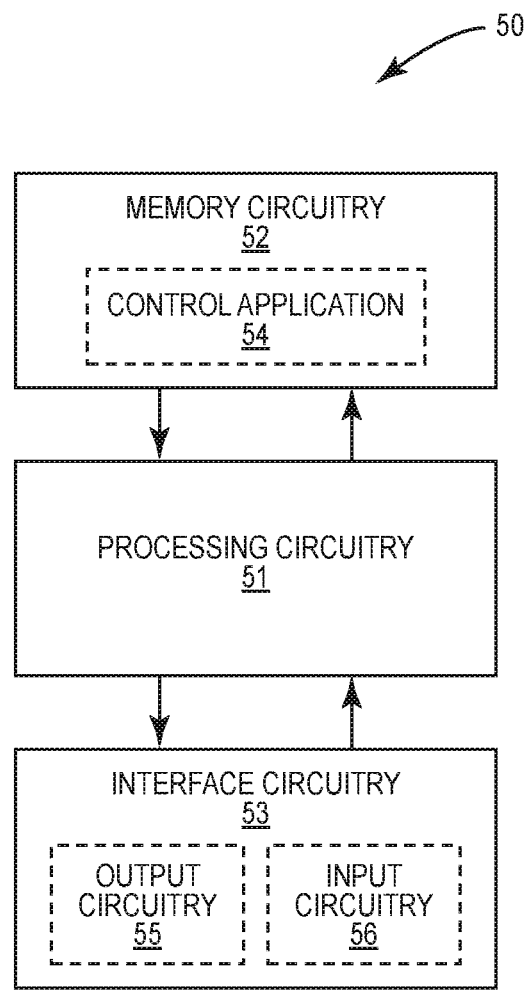
FIG. 5A is a schematic diagram of a computing device.

Other embodiments of the present disclosure include the computing device 50 implemented according to the hardware illustrated in FIG. 5A. The example hardware of FIG. 5A comprises processing circuitry 51, memory circuitry 52, and interface circuitry 53. Additional components such as the one or more sensors 30, 40, one or more emitters 20, clock 56, display 58, and input device 59 are configured to communicate with the computing device 50 through the interface circuitry 53.

The processing circuitry 51 is communicatively coupled to the memory circuitry 52 and the interface circuitry 53, e.g., via one or more buses. The processing circuitry 51 may comprise one or more microprocessors, microcontrollers, hardware circuits, discrete logic circuits, hardware registers, digital signal processors (DSPs), field-programmable gate arrays (FPGAs), application-specific integrated circuits (ASICs), or a combination thereof. For example, the processing circuitry 51 may be programmable hardware capable of executing software instructions stored as a machine-readable computer program 54 in the memory circuitry 52. The memory circuitry 52 of the various embodiments may comprise any non-transitory machine-readable media known in the art or that may be developed, whether volatile or non-volatile, including but not limited to solid state media (e.g., SRAM, DRAM, DDRAM, ROM, PROM, EPROM, flash memory, solid state drive, etc.), removable storage devices (e.g., Secure Digital (SD) card, miniSD card, microSD card, memory stick, thumb-drive, USB flash drive, ROM cartridge, Universal Media Disc), fixed drive (e.g., magnetic hard disk drive), or the like, wholly or in any combination.

The interface circuitry 53 may be a controller hub configured to control the input and output (I/O) data paths of the computing device 50. Such I/O data paths may include data paths for exchanging signals over a communications network and data paths for exchanging signals with a user. For example, the interface circuitry 53 may comprise a transceiver configured to send and receive communication signals over one or more of a cellular network, Ethernet network, or optical network. The interface circuitry 53 may also comprise one or more of a graphics adapter, display port, video bus, touchscreen, graphical processing unit (GPU), display port, Liquid Crystal Display (LCD), and Light Emitting Diode (LED) display, for presenting visual information to a user. The interface circuitry 53 may also comprise one or more of a pointing device (e.g., a mouse, stylus, touchpad, trackball, pointing stick, joystick), touchscreen, microphone for speech input, optical sensor for optical recognition of gestures, and keyboard for text entry.

The interface circuitry 53 may be implemented as a unitary physical component, or as a plurality of physical components that are contiguously or separately arranged, any of which may be communicatively coupled to any other, or may communicate with any other via the processing circuitry 51. For example, the interface circuitry 53 may comprise output circuitry 55 (e.g., transmitter circuitry configured to send communication signals over the communications network) and input circuitry 56 (e.g., receiver circuitry configured to receive communication signals over the communications network). Similarly, the output circuitry 55 may comprise a display, whereas the input circuitry 56 may comprise a keyboard. Other examples, permutations, and arrangements of the above and their equivalents will be readily apparent to those of ordinary skill.

According to embodiments of the hardware illustrated in FIG. 5A, the interface circuitry 51 is configured to receive signals from one or more sensors 30, 40. The processing circuitry 51 is configured to receive the signals and determine various aspects regarding the environment. This may include but is not limited to the processing circuitry 51 configured to perform calculations to determine various aspects such as but not limited to the skin temperature of a person, skin color, the number of people within the environment 100, the time each person has been in the environment, where within the environment each person has been, the use of protective equipment such as eye protection, the level of radiation emitted, and the amount of time that each emitter 20 has been activated.

Interface circuitry 53 may also provide communications with one or more of the emitters 20. Signaling between the interface circuitry 53 and the germicidal radiation emitter(s) 20 provides for the processing circuitry 51 of the computing device 50 to control the amount of germicidal radiation that is being emitted into the environment 100. The processing circuitry 51 may communicate with the sensors 30, 40 and emitter 20 in various manners, including various hardwire and wireless configurations.

Figure 5B:
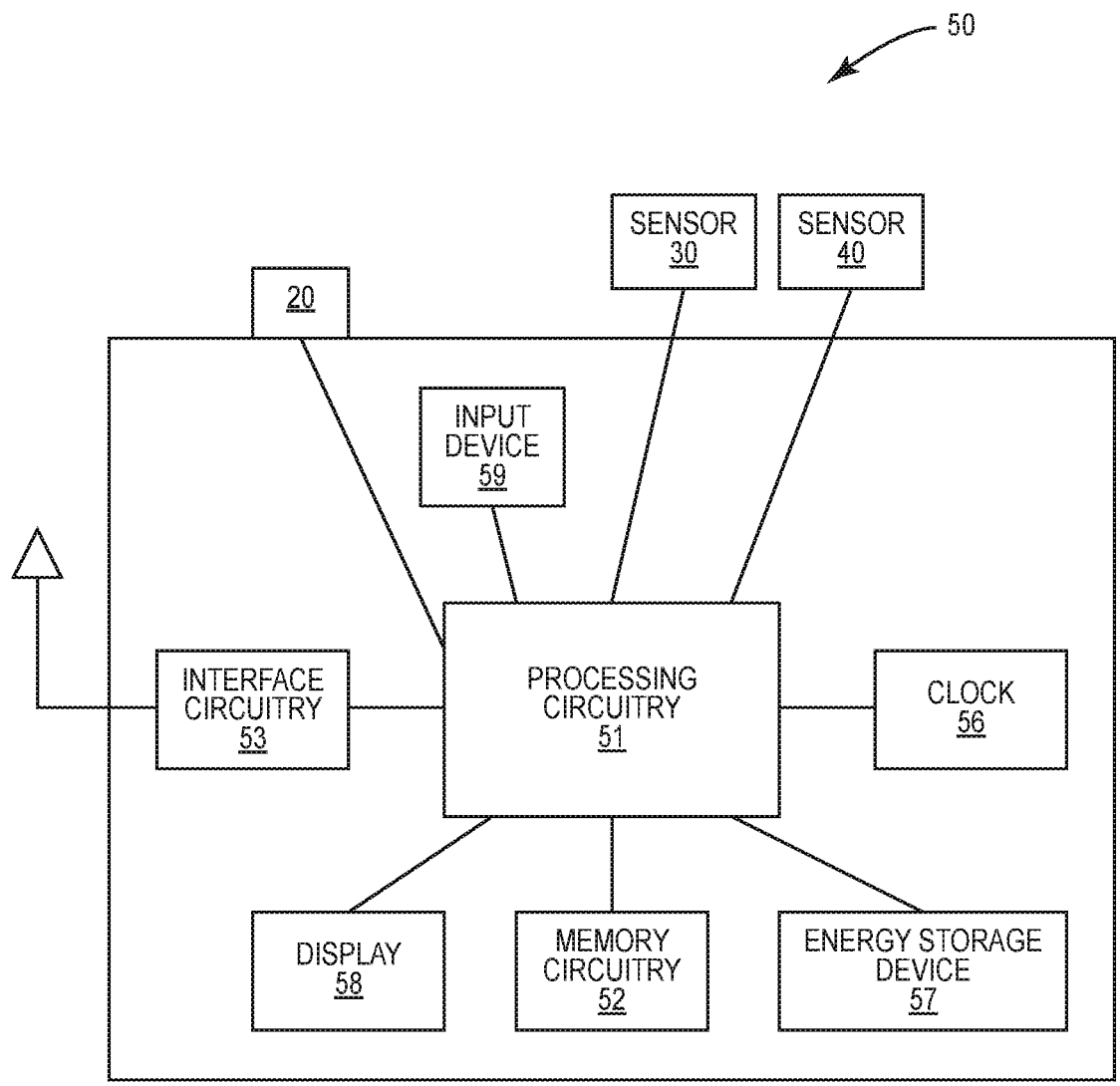
FIG. 5B is a schematic diagram of a computing device.

Other embodiments of the present disclosure include the computing device 50 as illustrated in FIG. 5B. The computing device 50 controls the operation of the system 10. As illustrated in FIG. 5B, the computing device 50 includes processing circuitry 51 that includes, for example, one or more microprocessors, microcontrollers, Application Specific Integrated Circuits (ASICs) or the like, configured with appropriate software and/or firmware to control the overall operation of the system 10 according to program instructions stored in the memory circuitry 52. The processing circuitry 51 is configured to perform calculations to determine various aspects such as but not limited to the skin temperature of a person, skin color, the number of people within the environment 100, the time each person has been in the environment, where within the environment each person has been, the use of eye protection, the level of radiation emitted from the one or more emitters 20, and the amount of time that each emitter 20 has been activated.

The computing device 50 includes a computer-readable storage medium (shown as memory circuitry 52), which stores instructions and/or data needed for operation. The memory circuitry 52 may include both volatile and non-volatile memory, for example.

The computing device 50 receives signals from various sources such as the one or more sensors 30, 40 regarding people within the environment 100 and protective equipment. The sensors 30, 40 may be separate components that are communicatively coupled to the computing device 50 as illustrated in FIG. 5B. Other embodiments may include the sensors 30, 40 included within the processing circuitry 51.

The interface circuitry 54 may comprise a short-range wireless interface, such as a BLUETOOTH interface, RFID, ZIGBEE, or WIFI interface, and a long range cellular phone or satellite communications interface. Interface circuitry 54 may also include an antenna configured for transmitting and receiving wireless signals to and from remote sources. The interface circuitry 54 may also be equipped to wirelessly communicate with the components within the environment such as sensors 30, 40, and germicidal radiation emitter(s) 20.

A clock 56 may be associated with the computing device 50 that measures the various timing requirements for specific events. The clock 56 may be independent from the processing circuitry 51 as illustrated in FIG. 5B, or may be incorporated within the processing circuitry 51. Clock 56 may interface through the interface circuitry 53 (see FIG. 5A).

An energy storage device 57 (e.g., a battery) is provided to power the various components of the computing device 50, such as the processing circuitry 51. In one embodiment, the energy storage device 57 is a battery. One or more of the components may also be configured to be wired into the power supply of the environment 100 in which it is mounted.

A display 58 may be configured to display information to a person or someone monitoring the system 10. The display 58 may comprise a liquid crystal display (LCD) or an organic light emitting diode (OLED) for example. An input 59 may provide for the input of information, such as a person entering into the environment 100 to enter identification. The input 59 may include a variety of formats, including but not limited to one or more buttons, touchpad, and keypad. The display 58 and/or the input 59 may interface through the interface circuitry 53 (see FIG. 5A).

The control signal from the processing circuitry 51 to the emitter 20 can be conveyed by hard wiring or conveyed wirelessly.

Figure 16:
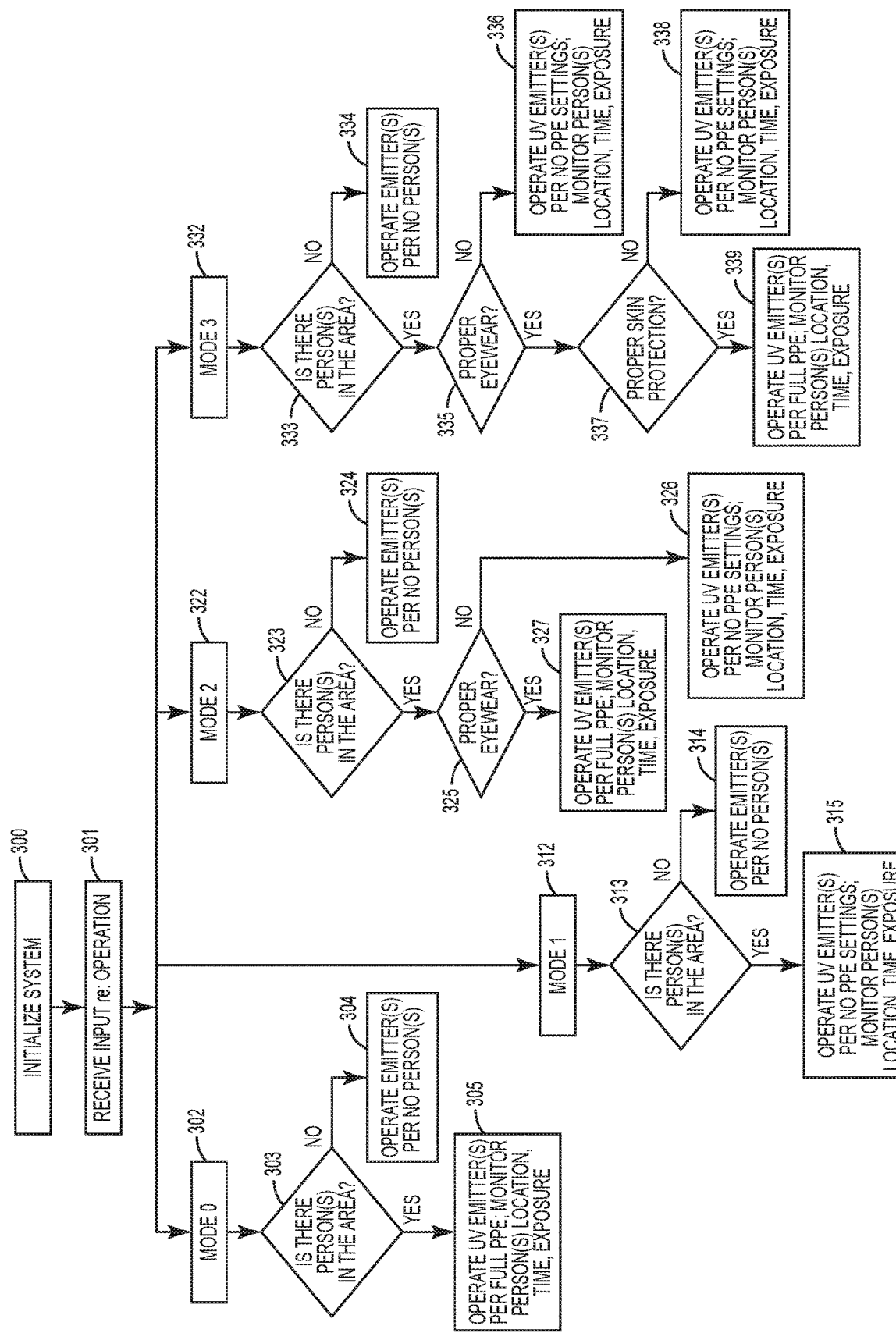
FIG. 16 is a flowchart diagram of a method of sanitizing an environment using germicidal radiation.

FIG. 16 illustrates one process of system operation to disinfect an environment 100. Prior to operation, the system 10 is initialized (block 300). The computing device 10 may perform an initial assessment of the various components of the system 10. This may include communicating with each of the various components (e.g. imaging system 30, sensors 40, emitters 20) to ensure each is in proper operational condition. In the event that a component is found to be non-operational, the processing circuitry 51 may prevent activation of the emitters 20 throughout the environment 100. Once the component becomes operational, the processing circuitry 51 may allow activation of the emitters 20. The processing circuitry 51 may also prevent initialization of just the section 110 that is directly affected by the non-operational component. Other sections 110 in which components are operational may be activated. Using the environment 100 of FIG. 2 as an example, when the processing circuitry 51 determines that a sensor 40 within room 110a is not operating properly, the processing circuitry 51 may prevent activation of the corresponding emitter 20 in that room 110a. If the other components in the environment 100 are determined to be operational, the computing device 50 may initialize the system 10 in these areas 110b, 110c, 110d.

The processing circuitry 51 then determines the operational mode (block 301). This may include an input received from the user, such as through an input device 59. The processing circuitry 51 may also be set to a default operational mode which is used unless an alternate operational mode is determined.

The processing circuitry 51 may be configured to operate in one of four different operational modes. The operational modes include different germicidal radiation emissions control schemes based on whether eye and/or skin protective equipment sensors are provided. Operational Modes 2 or 3 would be chosen when protective equipment is provided to persons. Operational Mode 0 or 1 is chosen depending upon whether or not protective equipment is assumed to be worn by the persons in the environment. These different Operational Modes can either be selected as an input from the user, or the processing circuitry 51 can be provided and installed pre-programmed. The processing circuitry 51 may also operate with fewer than four different operational modes such that one or more of the modes is not available.

environment without concern for exposed skin or head areas. The processing circuitry 51 may track the location of the one or more persons, and monitor their time in the germicidal radiation environment.

Operational Mode 0 may be useful for performing testing regarding the spread of contagious diseases and the effectiveness of germicidal radiation to control those diseases. This scenario may also be useful in an operating room or intensive care unit of a hospital. The processing circuitry 51 could collect data regarding the time that each individual was in the germicidal radiation exposure and where they were within the environment. Swabs could be taken, and statistically designed studies conducted to greatly enhance an understanding of how these diseases are spread and how effective continuous or semi-continuous germicidal radiation actually would be in disinfecting occupied areas. Operational Mode 0 may also be useful in situations where the imaging system 30 is not functioning adequately to differentiate "safe" and "unsafe" areas for direction controlled germicidal radiation exposure. Administrative controls are used to ensure that persons in the area have full eye and skin protection, and the processing circuitry 51 is able to decontaminate the environment using direction controlled germicidal radiation.

In Operational Mode 0, persons in an area where germicidal radiation is being emitted are tracked and are assumed by administrative controls to have adequate eye and skin protection.

| Operational Mode | Persons in Area | Eye Protection | Skin Protection |
| --- | --- | --- | --- |
| Operational Mode 0 | Monitored electronically with feedback into system | Assumed Adequate, administratively controlled | Assumed Adequate, administratively controlled |
| Operational Mode 1 | Monitored electronically with feedback into system | Assumed Inadequate | Assumed Inadequate |
| Operational Mode 2 | Monitored electronically with feedback into system | Monitored electronically with feedback into system | Assumed Adequate, administratively controlled |
| Operational Mode 3 | Monitored electronically with feedback into system | Monitored electronically with feedback into system | Monitored electronically with feedback into system |

Operational Mode 0 (block 302) operates under the assumption that persons in the area are protected from germicidal radiation exposure (protected=adequate eye and skin protection administratively controlled). The processing circuitry 51 determines if there are any persons in the area (block 303). If there are no persons, the processing circuitry 51 operates the emitters 20 at prescribed settings (block 304) suited for no persons in the area. This mode of operation with no persons present may provide for more intense germicidal radiation exposure for more thorough decontamination or less germicidal radiation exposure to save energy costs, or a combination of more intense radiation for a period of time followed by less intense exposure to save costs. The emitters 20 may be operated continuously, or may be pulsed with periods of high radiation emission followed by periods of low or no radiation emission. The desired emission durations and frequencies will vary depending on the environment being decontaminated, the organisms being treated, and user preferences.

If there is a person in the area (block 303), the emitters 20 emit germicidal radiation per prescribed settings for persons wearing full PPE (block 305). This may include high power decontamination of the environment and persons in the Operational Mode 1 (block 312) operates under the assumption that one or more persons in the area are not protected from germicidal radiation exposure. If the processing circuitry 51 determines that there are no persons in the area (block 313), the emitters 20 operate at prescribed settings for no persons in the area (block 314) as described above. If there are one or more persons (block 313), the locations of the persons may be tracked and the time and germicidal radiation exposure for each person monitored (block 315). In this mode, imaging system 30 scans the area, the processing circuitry 51 determines "safe" and "unsafe" areas and then controls at least one of the direction, intensity, and shape of the germicidal radiation emitted into the environment by emitters 20 onto areas that have been determined by the processing circuitry to be safe and does not emit germicidal radiation onto areas determined by the processing circuitry 51 to be unsafe (e.g. exposed skin or head areas). This mode may use sensors 40 configured to track the location of persons in the area to anticipate the movements of persons throughout the area to improve both the safety of persons in the environment and the decontamination of the environment.

Operational Mode 2 (block 322) includes monitoring for eye protection for persons in the environment using sensor 40, and skin protection is assumed to not be adequate as in Operational Mode 1. In this mode, as in Operational Mode 1, the imaging system 30 scans the environment, the processing circuitry 51 determines "safe" and "unsafe" areas and then controls the direction, intensity, and shape of the germicidal radiation emitted into the environment by emitters 20 onto areas that have been determined by the processing circuitry to be "safe" and does not emit germicidal radiation onto areas determined by the processing circuitry to be "unsafe" (e.g. exposed skin or head areas or persons in the environment). The difference between this mode and Mode 1, however, is that in this mode, the processing circuitry 51 can be configured to not emit germicidal radiation into the environment or section of the environment in which the person who is not wearing eye protection is located. Alternatively, the processing circuitry 51 can be configured to increase the areas that are considered unsafe and not emit direction controlled germicidal radiation within a certain number of feet from the person who is not wearing the eye protection.

If there are no persons in the area (block 323), the emitters 20 operate per prescribed settings (block 324) as described above. If it is determined that there is one or more persons in the area (block 323), the processing circuitry 51 determines whether they are wearing eye protection (block 325). If the person does not have eye protection, the emitters 20 may also shut down immediately. In one embodiment, the processing circuitry 51 may provide a time delay and warning, such as a voice that requests person in the area to check their eye protection and make certain it is properly worn. In another embodiment, the processing circuitry 51 may cut back the level of emissions to threshold limit value levels (block 326), or the processing circuitry 51 may increase the "unsafe" area around the person with no eye protection. If the persons have eye protection, as determined by smart PPE and PPE sensors described in detail in this application, the emitters 20 emit germicidal radiation per prescribed settings (block 327). Operational Mode 2 is particularly useful in situations where there are concerns about the efficacy of the system to keep the germicidal radiation off of the head and eyes in particular. This mode is also particularly useful in situations where there are concerns about germicidal radiation reflecting off of objects in the environment or off of the surfaces of the environment (walls, floors, etc.) and coming in contact with the eyes.

Methods for protecting the eyes of people in an environment of germicidal radiation may employ various forms of protection not currently available. For example, small, unobtrusive switches or sensors located in the eyewear nose pieces, bridge, frame, strap, etc., could detect whether or not the eyewear is properly fitted on the head. For example, in the case of protective glasses, small switches or pressure sensors could be mounted in the nose piece and behind the head in an elastic strap. When the eyewear is in position and held in place with tension on the strap, both front and rear switches or sensors detect pressure, and these in turn communicate through a wireless transmitter (or a physical wire for persons that are relatively immobile) in the eyewear to the processing circuitry 51 indicating proper donning of the protective eyewear. Similarly, pressure sensors may be included on a strap used to secure the protective equipment to the person. If the pressure sensed is below a predetermined amount, the processing circuitry 51 interprets that the equipment is not being worn properly.

Operational Mode 3 (block 332) includes monitoring for eye and skin protection for persons in the environment using sensor 40. In this mode, as in Operational Modes 1 and 2, the imaging system 30 scans the environment and the processing circuitry 51 determines "safe" and "unsafe" areas. The processing circuitry 51 then controls at least one of the direction, intensity, or shape of the germicidal radiation emitted into the environment by emitters 20 onto areas that have been determined to be safe and does not emit germicidal radiation onto areas determined to be unsafe (e.g. exposed skin or head areas or persons in the environment). The difference between this mode and Modes 1 and 2 is that in this mode, the processing circuitry 51 can be configured to not emit any germicidal radiation into the environment or section of the environment in which the person who is not wearing eye protection or skin is located. Alternatively, the processing circuitry 51 can be configured to increase the areas that are considered "unsafe" and not emit any direction controlled germicidal radiation within say a certain number of feet from the person who is not wearing the eye protection or the person who is not wearing the skin protection.

If there are no persons in the area (block 333), the emitters 20 operate per prescribed settings (block 334) as described above. If it is determined that there is one or more persons in the area (block 333), the processing circuitry 51 determines whether they are wearing eye protection (block 335). If the person does not have eye protection, the emitters 20 may also shut down immediately. Alternatively, the processing circuitry 51 may institute a delay and provide a audible warning such as a voice that requests person in the area to check their eye protection and make certain it is properly worn. If the one or more persons still do not have eye protection, the processing circuitry 51 may cut back the level of emissions to threshold limit value levels, or the processing circuitry may increase the "unsafe" area around the person with no eye protection (block 336).

If there is proper eye protection, the processing circuitry 51 detects for skin protection (block 337). If there is no adequate skin protection, the emitters 20 may shut down immediately or cut back to threshold limit value levels (block 338). Alternatively, the processing circuitry 51 can be configured to increase the areas that are considered "unsafe" and not emit any direction, intensity, or shape controlled germicidal radiation within say a certain number of feet from the person who is not wearing the skin protection.

If there is proper skin protection, the emitter 20 emits germicidal radiation per prescribed settings (block 339). This may include emitting radiation onto the protected skin. In this third mode, if the protective eyewear comes off or the cameras with computer analysis detect skin that is not adequately protected, the emitter 20 is cut back accordingly to a safe level. In another embodiment of Operational Mode 3, eye protection sensors are not provided and are assumed to be adequate and controlled administratively, and only skin protection monitoring is provided. In yet another embodiment of Operational Mode 3, video monitoring and computer analysis of the images determines whether both eye and skin protection are properly donned to protect the individuals from germicidal radiation exposure.

Operational Mode 3 is particularly useful in situations where the full decontamination in the environment is desired, including the protected skin of persons in the environment. In situations where full skin covering with radiation blocking fabrics and materials is not desired, yet maximum decontamination is required, simply applying a sunscreen lotion on the skin periodically to block harmful germicidal radiation such as UV radiation is sufficient, and the circuitry can be set to decontaminate even bare skin if the lotion is detected. Furthermore, germ killing additives can be added to the lotion for further biocidal activity. This potential combination of using both germicidal radiation and germicidal lotions on the skin of persons in the environment makes Mode 3 the mode that has the potential to achieve the highest degree of decontamination of the environment and persons in the environment. Mode 3 is also particularly useful in situations where there are concerns about germicidal radiation reflecting off of objects in the environment or off of the surfaces of the environment (walls, floors, etc.) and coming in contact with the eyes and skin. The direction controlled germicidal radiation can be kept off of the skin by means already described, yet protective coatings are used on the skin and monitored just in case.

The control signal from the processing circuitry 51 to the germicidal light source 20 can be conveyed by hard wiring or conveyed wirelessly. Wireless control signals have several benefits. First, the installation costs should be significantly lower than hard wiring. Second, temporary systems can be installed and removed without making any holes in walls and ceilings, etc.

The processing circuitry 51 may also be configured to adjust the germicidal radiation emissions and or the modes of operation through auditory signals. The system 10 includes one or more noise sensors in the environment that is able to detect noises and speech. The processing circuitry 51 is configured to change the emission based on this detected information. In one embodiment, the processing circuitry 51 is configured to receive voice commands to adjust the settings. Other noises such as coughing or sneezing may also cause a change in emissions or the areas that the system prioritizes for decontamination.

The eye protection worn by persons in the area may be equipped with additional features. One feature includes a display and/or LED lights that are mounted in one corner of the eye protection. This indicates to the wearer whether or not the PPE is properly worn. Another feature is an audible voice or alarm tone that can be used to communicate to the wearer or local nursing staff when the PPE is first donned properly and when it comes off. The equipment may also include a microphone to allow the person to communicate voice commands that are transmitted wirelessly by a transmitter to the processing circuitry 51. This may include control commands such as "turn off UV", or "UV low" or "UV high". Other voice activated controls may also be included, such as room lighting, television activation and channel, and nurse calling. The equipment may also include one or more sensors to monitor the person, such as blood pressure, heart rate, and other data of interest.

If the beam of light can be seen in the air as it travels through the environment from the emitter to the surface it is being direct towards, it is usually do to dust or particulates, even moisture droplets, smoke, etc., suspended in the air. When germicidal radiation is used, microbes suspended in the air from shaking bedding, walking around, coughing, etc., may rise into the beam and be exposed to the radiation and be disinfected. Thus, being able to disinfect the air through which the beam travels is a useful feature of this invention.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise. The present invention may be carried out in other specific ways than those herein set forth without departing from the scope and essential characteristics of the invention. The present embodiments are, therefore, to be considered in all respects as illustrative and not restrictive.

What is claimed is:

1. A system for disinfecting an environment, the system comprising:
   an imaging system configured to capture an image of an environment;
   a germicidal radiation emitter that emits germicidal radiation into the environment; and
   processing circuitry configured to:
      analyze the image of the environment and determine an area within the environment either where a person is located or where exposed skin of the person in the environment is located;
      adjust at least one of a shape of a beam that is emitted by the emitter, an intensity of the germicidal radiation, and a direction of the germicidal radiation to prevent the germicidal radiation from being emitted into the environment in the area where the person is located or where the exposed skin is located,
      wherein the processing circuitry is further configured to track movement of the person in the environment.

2. The system of claim 1, wherein the processing circuitry is further configured to detect whether the person in the environment is wearing eye protection and to prevent the germicidal radiation emitter from emitting the germicidal radiation onto the person or onto a head of the person when the person is not wearing the eye protection.

3. The system of claim 1, wherein the processing circuitry is further configured to detect whether the person in the environment is wearing a protective coating on the exposed skin that is not protected by clothing.

4. The system of claim 1, further comprising a means of calibrating a direction control mechanism for adjusting a direction that the germicidal radiation emitter emits the germicidal radiation.

5. The system of claim 1, wherein the imaging system comprises a plurality of cameras, wherein at least two cameras of the plurality of cameras are configured to capture images of the environment based on different wavelengths of a radiation spectrum, including at least two of ultraviolet, visible, and infrared wavelengths.

6. A system for disinfecting an environment, the system comprising:
   a germicidal radiation emitter that emits hazardous levels of germicidal radiation into the environment;
   at least one camera that captures an image of the environment; and
   processing circuitry configured to:
      analyze the image of the environment and determine a first area in the environment where the hazardous levels of the germicidal radiation can be emitted and cause the germicidal radiation emitter to emit the hazardous levels of the germicidal radiation in the first area;
      analyze the image of the environment and determine a second area in the environment where a person is located and where less than the hazardous levels of the germicidal radiation can be emitted and cause the germicidal radiation emitter to emit less than the hazardous levels of the germicidal radiation in the second area, wherein the processing circuitry is further configured to track movement of the person in the environment.

7. The system of claim 6, wherein the processing circuitry is further configured to detect whether the person in the environment is wearing eye protection and to prevent the germicidal radiation emitter from emitting the hazardous levels of the germicidal radiation onto the person or a head of the person when the person is not wearing the eye protection.

8. The system of claim 6, wherein the processing circuitry is further configured to detect whether the person in the environment is wearing a protective coating on exposed skin that is not protected by clothing.

9. The system of claim 6, wherein the system comprises a plurality of cameras, wherein at least two cameras of the plurality of cameras are configured to capture images of the environment based on different wavelengths of a radiation spectrum, including at least two of ultraviolet, visible, and infrared wavelengths.

\* \* \* \* \*